United States Patent
Yu et al.

(10) Patent No.: US 10,153,436 B2
(45) Date of Patent: Dec. 11, 2018

(54) COMPOUND FOR AN ORGANIC OPTOELECTRONIC ELEMENT, ORGANIC LIGHT-EMITTING ELEMENT COMPRISING SAME, AND DISPLAY DEVICE COMPRISING THE ORGANIC LIGHT-EMITTING ELEMENT

(71) Applicant: CHEIL INDUSTRIES INC., Kyungsangbuk-do (KR)

(72) Inventors: Eun-Sun Yu, Uiwang-si (KR); Moo-Jin Park, Uiwang-si (KR); Ho-Jae Lee, Uiwang-si (KR); Mi-Young Chae, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 691 days.

(21) Appl. No.: 14/358,346

(22) PCT Filed: Sep. 25, 2012

(86) PCT No.: PCT/KR2012/007706
§ 371 (c)(1),
(2) Date: May 15, 2014

(87) PCT Pub. No.: WO2013/094854
PCT Pub. Date: Jun. 27, 2013

(65) Prior Publication Data
US 2014/0346483 A1 Nov. 27, 2014

(30) Foreign Application Priority Data
Dec. 23, 2011 (KR) .................. 10-2011-0141434

(51) Int. Cl.
*H01L 51/54* (2006.01)
*C09K 11/06* (2006.01)
*H01L 51/00* (2006.01)
*C07D 333/76* (2006.01)
*C07D 209/82* (2006.01)
(Continued)

(52) U.S. Cl.
CPC ........ *H01L 51/0067* (2013.01); *C07D 209/82* (2013.01); *C07D 333/76* (2013.01); *C07D 471/04* (2013.01); *C07D 491/04* (2013.01); *C07D 495/04* (2013.01); *C09K 11/06* (2013.01); *H01L 51/0071* (2013.01); *H01L 51/0072* (2013.01); *H01L 51/5012* (2013.01); *H01L 51/5056* (2013.01); *H01L 51/5088* (2013.01); *H05B 33/14* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0081* (2013.01); *H01L 51/0085* (2013.01); *H01L 51/0504* (2013.01);

*H01L 51/42* (2013.01); *H01L 2251/308* (2013.01); *Y02E 10/549* (2013.01); *Y02P 70/521* (2015.11)

(58) Field of Classification Search
CPC ..... Y02E 10/549; Y02P 70/521; H05B 33/14; C07D 209/82; C07D 333/76; C07D 471/00; C07D 471/02; C07D 471/04; C07D 491/00; C07D 491/02; C07D 491/04; C07D 495/00; C07D 495/02; C07D 495/04; C09K 11/06; C09K 2211/00; C09K 2211/10; C09K 2211/1018; C09K 2211/1044; C09K 2211/1029; C09K 2211/1033; C09K 2211/1027; C09K 2211/1059; C09K 2211/1088; C09K 2211/1092; H01L 2251/308; H01L 51/0032; H01L 51/005; H01L 51/0051; H01L 51/0062; H01L 51/0067; H01L 51/0071; H01L 51/0072; H01L 51/0073; H01L 51/0081; H01L 51/0085; H01L 51/0504; H01L 51/42; H01L 51/50; H01L 51/5012; H01L 51/5016; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35; 544/212, 331; 546/276.7

See application file for complete search history.

(56) References Cited

U.S. PATENT DOCUMENTS 5,942,340 A † 8/1999 Hu
2002/0037427 A1 3/2002 Taguchi
(Continued)

FOREIGN PATENT DOCUMENTS

CN 1780897 A 5/2006
CN 102017220 A 4/2011
(Continued)

OTHER PUBLICATIONS

Search Report dated Jan. 27, 2015 in corresponding Chinese Patent Application No. 2012800595548.
(Continued)

*Primary Examiner* — Andrew K Bohaty
(74) *Attorney, Agent, or Firm* — Lee & Morse, P.C.

(57) ABSTRACT

Disclosed are a compound for an organic optoelectronic device, an organic light emitting diode including the same, and a display device including the organic light emitting diode. The compound for an organic optoelectronic device represented by a combination of the following Chemical Formula 1; and Chemical Formula 2 or 3 provides an organic light emitting diode having life-span characteristics due to excellent electrochemical and thermal stability, and high luminous efficiency at a low driving voltage.

10 Claims, 5 Drawing Sheets

(51) Int. Cl.
*H05B 33/14* (2006.01)
*C07D 471/04* (2006.01)
*C07D 491/04* (2006.01)
*C07D 495/04* (2006.01)
*H01L 51/50* (2006.01)
*H01L 51/05* (2006.01)
*H01L 51/42* (2006.01)

(56) References Cited

U.S. PATENT DOCUMENTS

| | | | |
|---|---|---|---|
| 2009/0096356 A1* | 4/2009 | Murase | C09K 11/06 |
| | | | 313/504 |
| 2009/0302742 A1 | 12/2009 | Komori et al. | |
| 2009/0309488 A1 | 12/2009 | Kato et al. | |
| 2010/0187977 A1 | 7/2010 | Kai et al. | |
| 2011/0062429 A1† | 3/2011 | Kai | |
| 2011/0309345 A1† | 12/2011 | Balaganesan | |
| 2012/0001165 A1 | 1/2012 | Komori et al. | |
| 2012/0097899 A1* | 4/2012 | Parham | C07D 401/04 |
| | | | 252/500 |

FOREIGN PATENT DOCUMENTS

| | | | | |
|---|---|---|---|---|
| CN | 104011893 A | 8/2014 | | |
| EP | 0906947 A1 | 9/1998 | | |
| EP | 2284920 A1 | 4/2009 | | |
| EP | 2416397 A1 | 3/2010 | | |
| JP | 2009-263579 A | 11/2009 | | |
| KR | 10-2009-0028357 A | 3/2009 | | |
| WO | WO 2010/113755 A | 10/2010 | | |
| WO | WO 2010/131855 A2 | 11/2010 | | |
| WO | WO-2011000455 A1 * | 1/2011 | ........... | C07D 401/04 |
| WO | WO-2011/019156 A1 | 2/2011 | | |
| WO | WO-2011/055934 A2 | 5/2011 | | |
| WO | WO 2011/108902 A2 | 9/2011 | | |

OTHER PUBLICATIONS

Chinese Search Report dated Sep. 16, 2015 in Corresponding Chinese Patent Application No. 201280059554.8.
Notice of Opposition dated Jun. 12, 2017, of the corresponding European Patent Application No. 12860332.1.

\* cited by examiner
† cited by third party

COMPOUND FOR AN ORGANIC OPTOELECTRONIC ELEMENT, ORGANIC LIGHT-EMITTING ELEMENT COMPRISING SAME, AND DISPLAY DEVICE COMPRISING THE ORGANIC LIGHT-EMITTING ELEMENT

TECHNICAL FIELD

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

BACKGROUND ART

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

DISCLOSURE

Technical Problem

A compound for an organic optoelectronic device that may act as a hole injection and transport material or an electron injection and transport material, and also act as a light emitting host along with an appropriate dopant is provided.

An organic light emitting diode having excellent lifespan, efficiency, driving voltage, electrochemical stability, and thermal stability and a display device including the same are provided.

Technical Solution

In one embodiment of the present invention, a compound for an organic optoelectronic device represented by a combination of the following Chemical Formula 1; and Chemical Formula 2 or 3 is provided. [Chemical Formula 1] [Chemical Formula 2] [Chemical Formula 3]

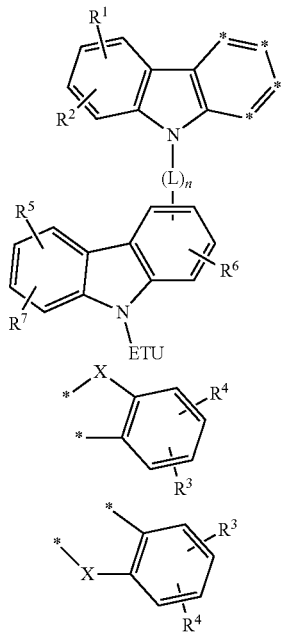

In the above Chemical Formulae 1 to 3, X is —O—, —S—, —NR'—, —S(O$_2$)—, —P(O)—, or —C(O)—, wherein R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, two *'s of the above Chemical Formula 1 are bonded with the adjacent two *'s of the above Chemical Formula 2 or 3 to form a fused ring, ETU is a substituted or unsubstituted C2 to C30 heteroaryl group having electron characteristics, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

The compound for an organic optoelectronic device may be represented by the following Chemical Formula 4.

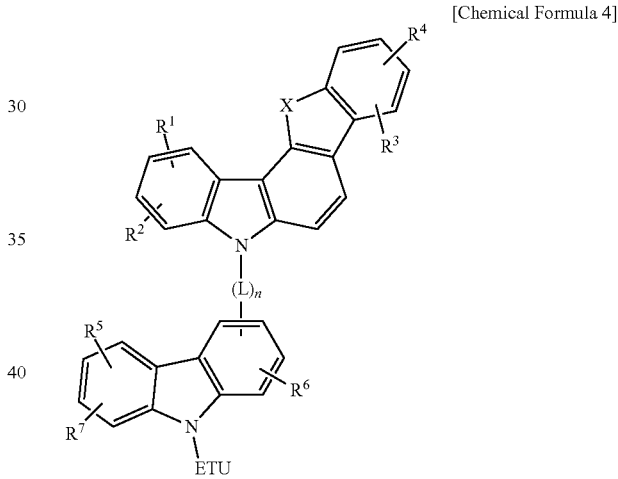

[Chemical Formula 4]

In the above Chemical Formula 4, X is —O—, —S—, —NR'—, —S(O$_2$)—, —P(O)—, or —C(O)—, R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, ETU is a substituted or unsubstituted C2 to C30 heteroaryl group having electron characteristics, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

The compound for an organic optoelectronic device may be represented by the following Chemical Formula 5.

[Chemical Formula 5]

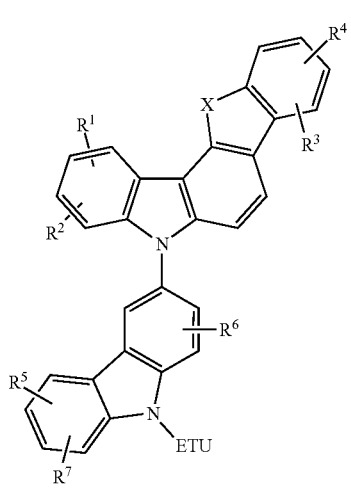

In the above Chemical Formula 5, X is —O—, —S—, —NR'—, —S(O$_2$)—, —P(O)—, or —C(O)—, wherein R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and ETU is a substituted or unsubstituted C2 to C30 heteroaryl group having electron characteristics.

The X may be —O— or —S—.

The ETU may be a substituted or unsubstituted pyridinyl group, a substituted or unsubstituted pyrimidinyl group, a substituted or unsubstituted triazinyl group, or a combination thereof.

The ETU may be a substituent represented by one of the following Chemical Formulae 6 to 10.

[Chemical Formula 6]

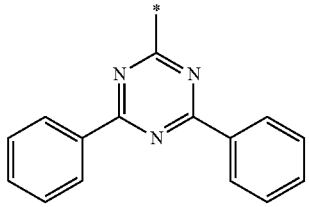

[Chemical Formula 7]

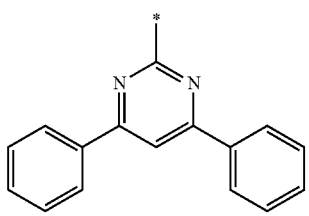

[Chemical Formula 8]

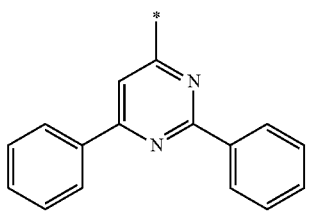

[Chemical Formula 9]

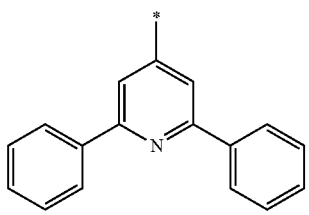

[Chemical Formula 10]

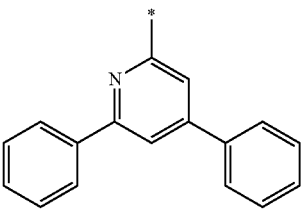

The compound for an organic optoelectronic device may be represented by one of the following Chemical Formulae A-1 to A-18.

[Chemical Formula A-1]
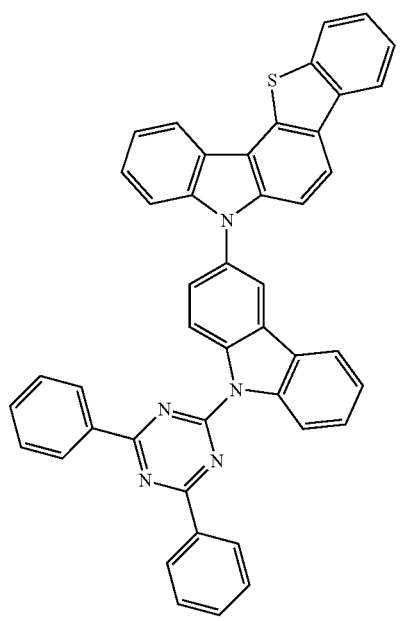
[Chemical Formula A-2]
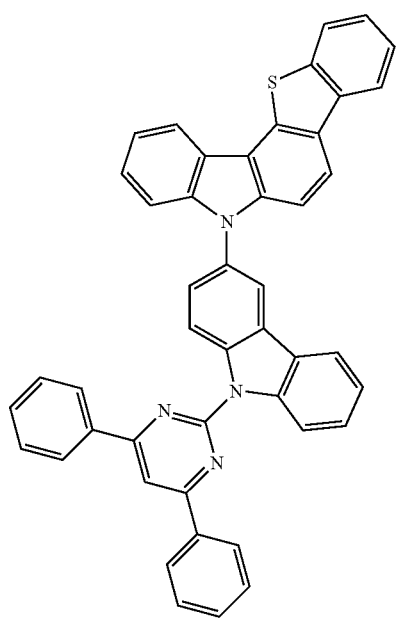
[Chemical Formula A-3]
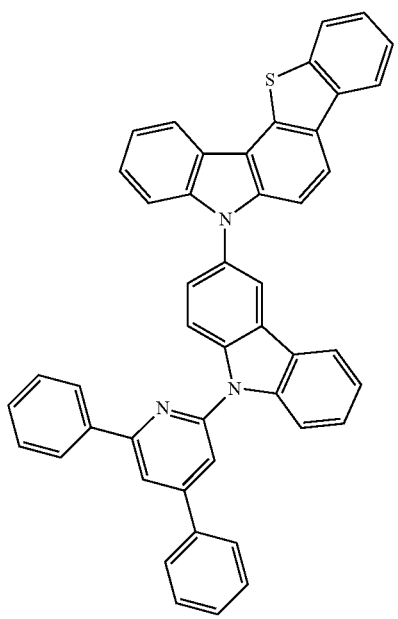
[Chemical Formula A-4]
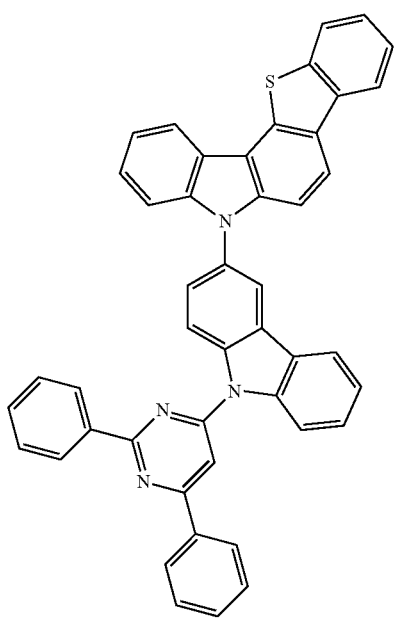

[Chemical Formula A-5]
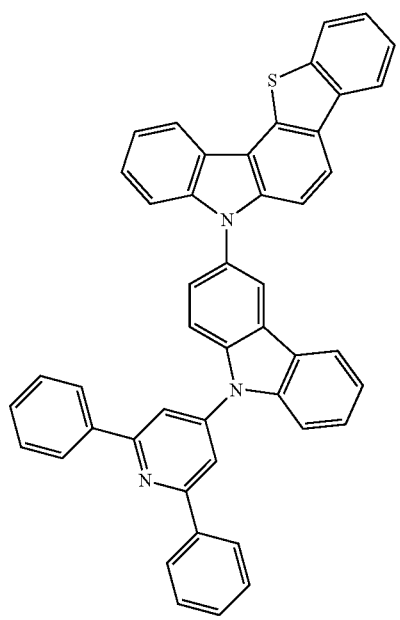
[Chemical Formula A-7]
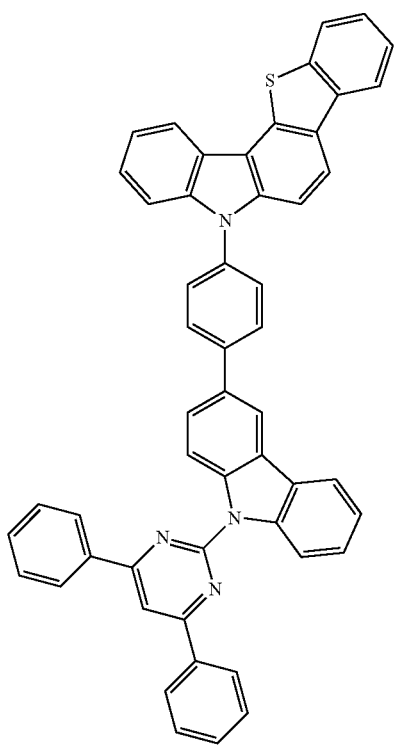
[Chemical Formula A-6]
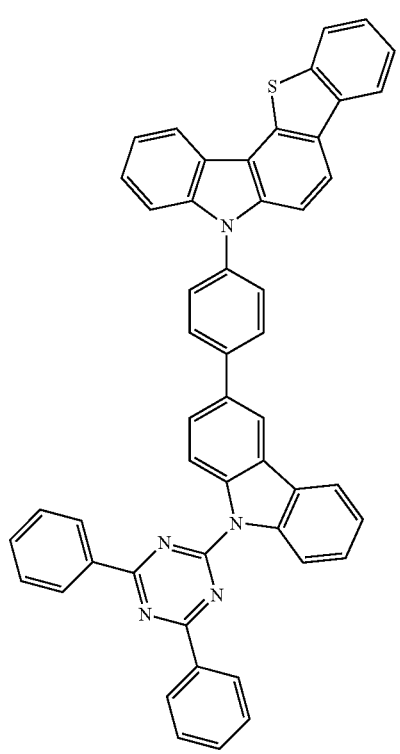
[Chemical Formula A-8]
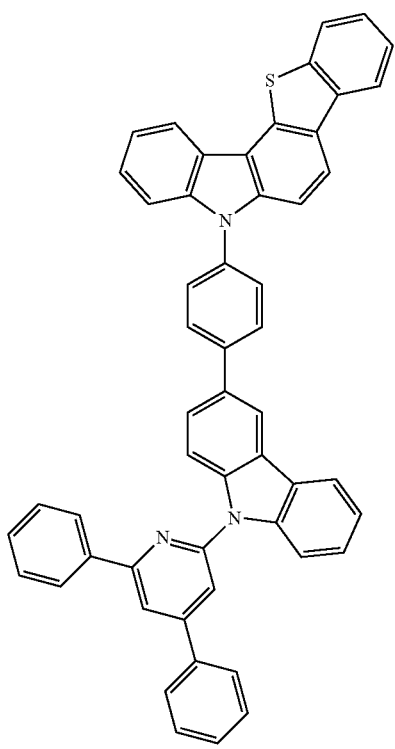

[Chemical Formula A-9]
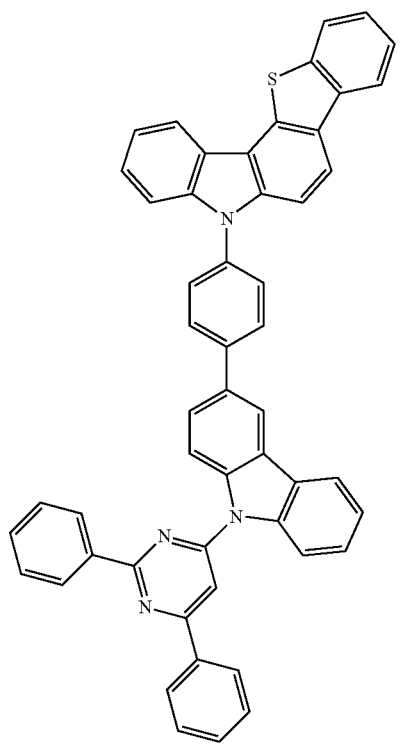
[Chemical Formula A-11]
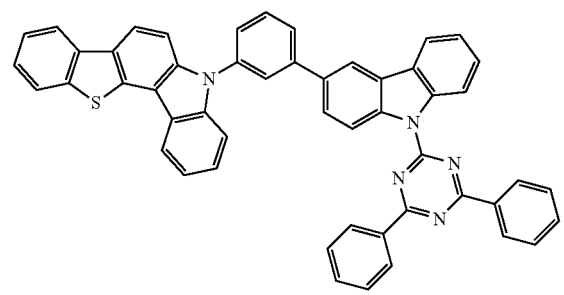
[Chemical Formula A-12]
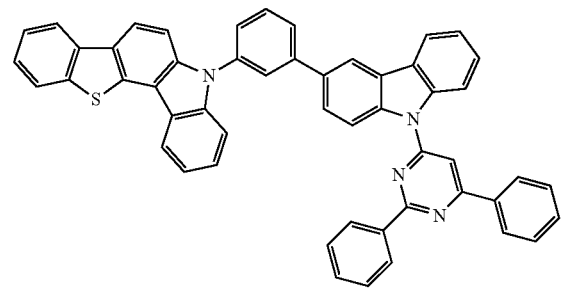
[Chemical Formula A-13]
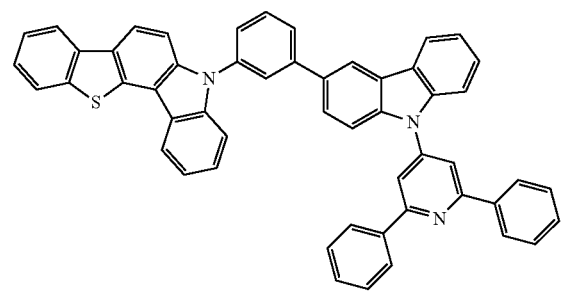
[Chemical Formula A-10]
[Chemical Formula A-14]
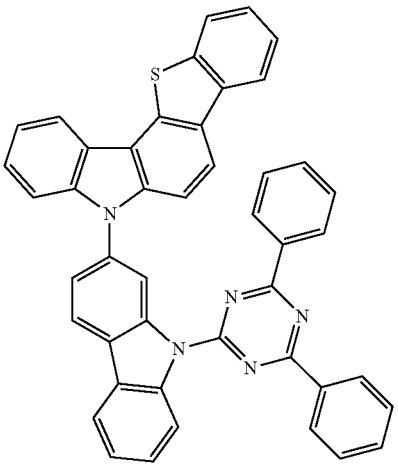

[Chemical Formula A-15]
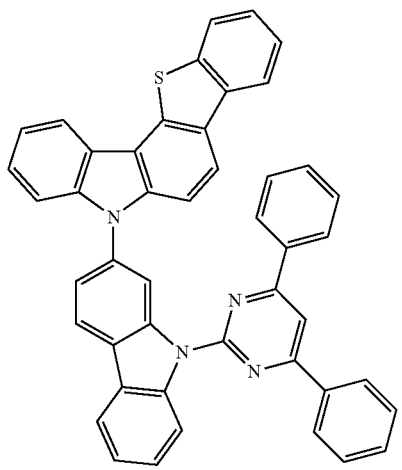
[Chemical Formula A-18]
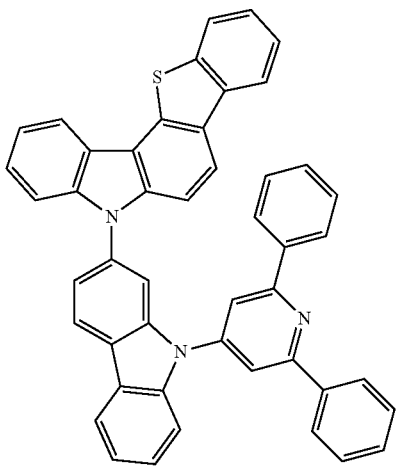
[Chemical Formula A-16]
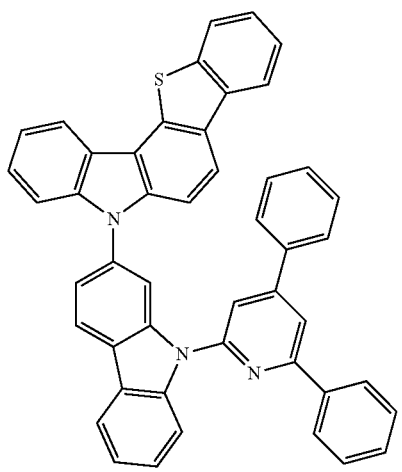
[Chemical Formula A-17]
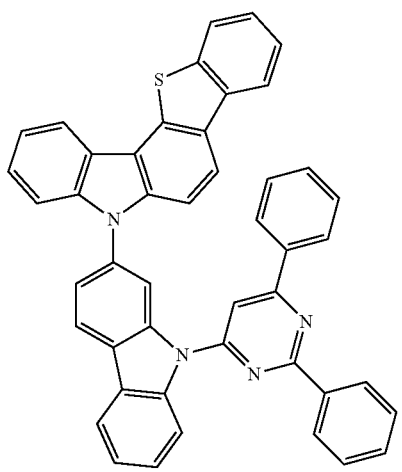
The compound for an organic optoelectronic device may be represented by one of the following Chemical Formulae B-1 to B-18.
[Chemical Formula B-1]
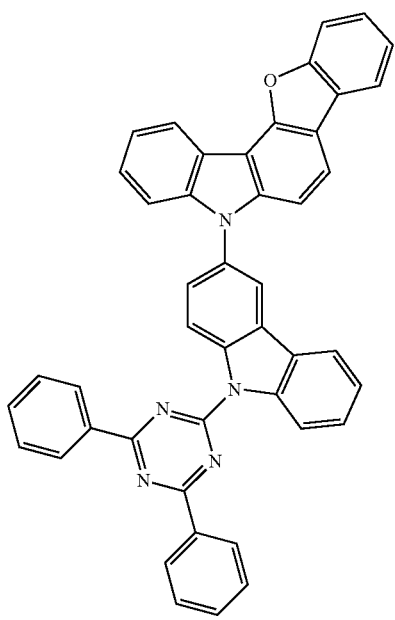

[Chemical Formula B-2]
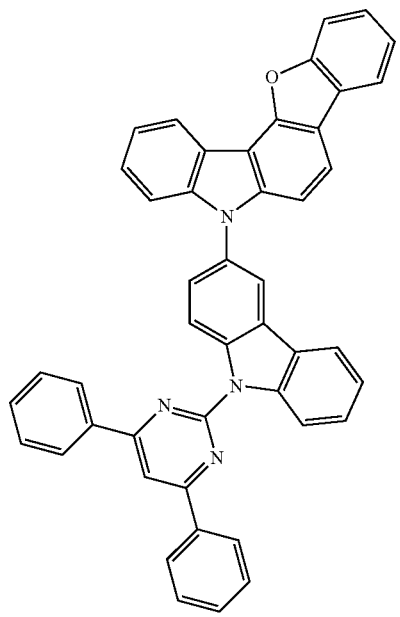
[Chemical Formula B-4]
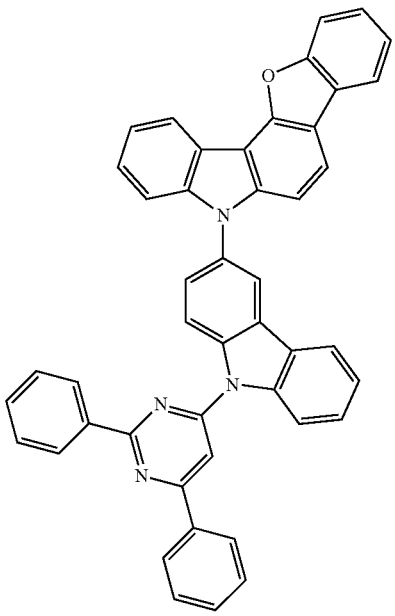
[Chemical Formula B-3]
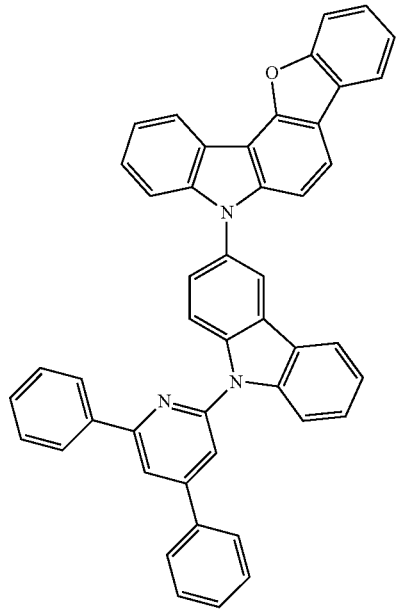
[Chemical Formula B-5]

[Chemical Formula B-6]
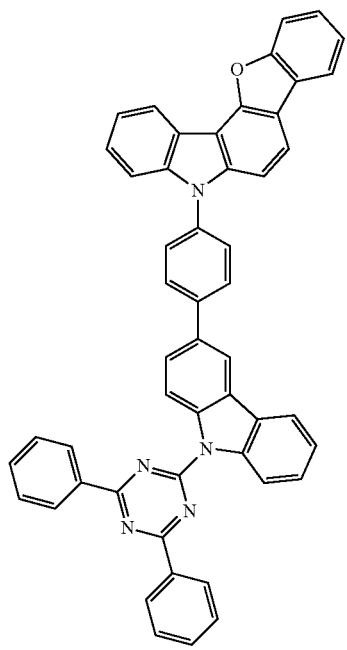
[Chemical Formula B-7]
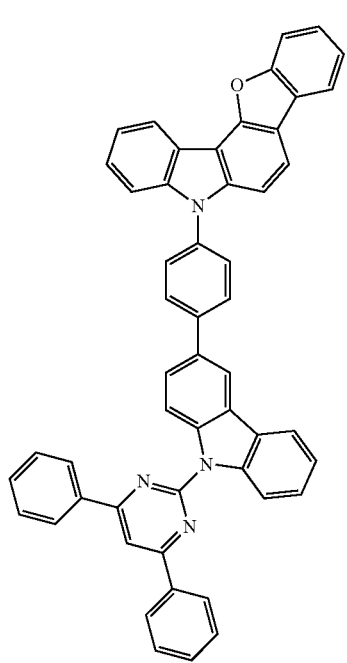
[Chemical Formula B-8]
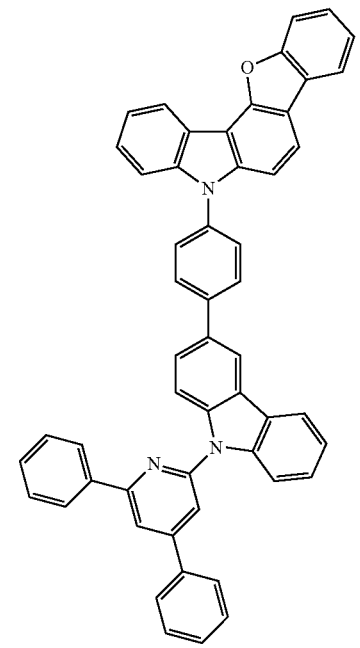
[Chemical Formula B-9]
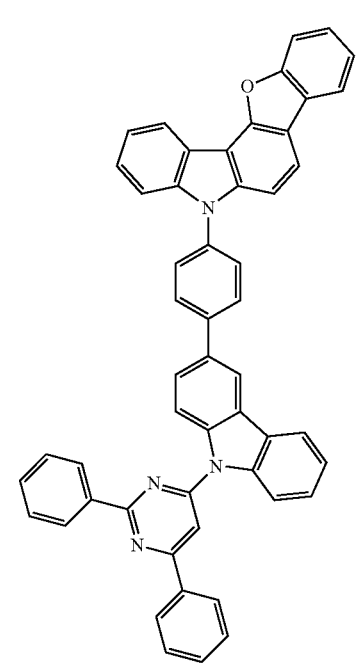

[Chemical Formula B-10]
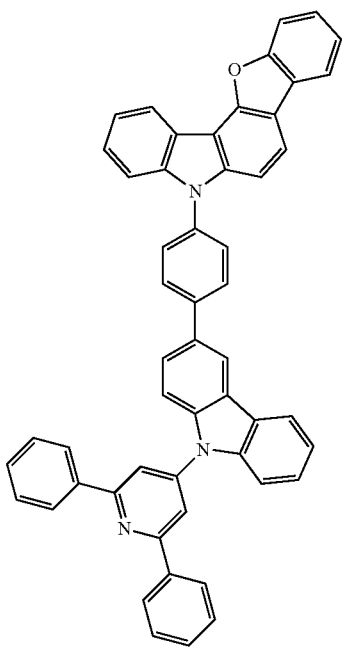
[Chemical Formula B-11]
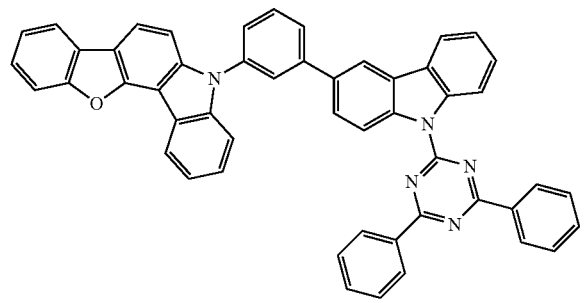
[Chemical Formula B-12]
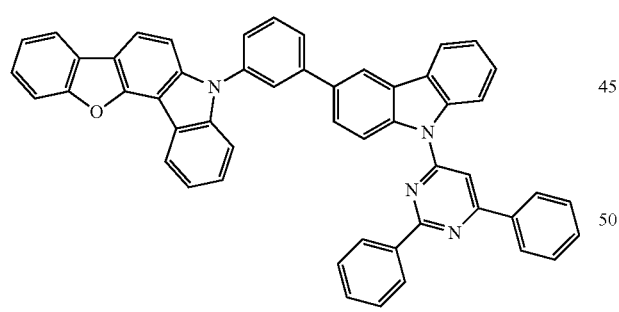
[Chemical Formula B-13]
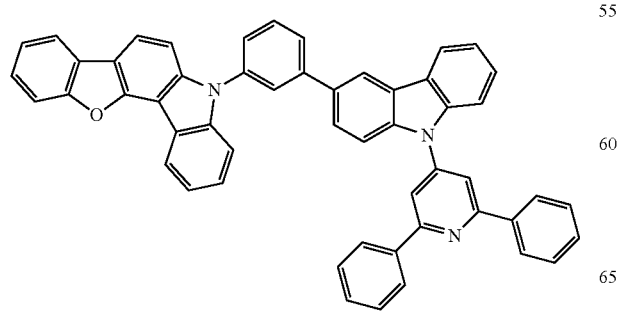
[Chemical Formula B-14]
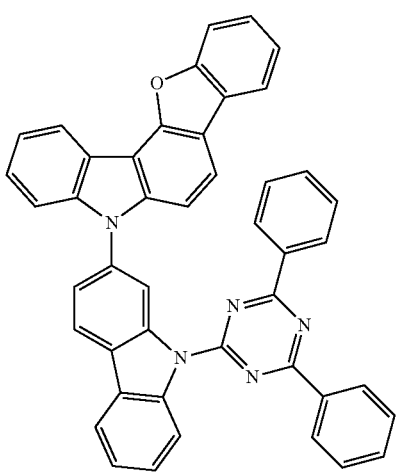
[Chemical Formula B-15]
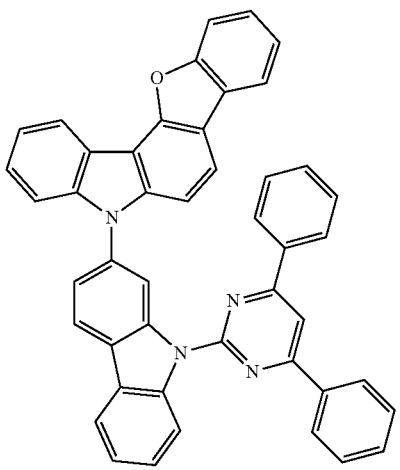
[Chemical Formula B-16]
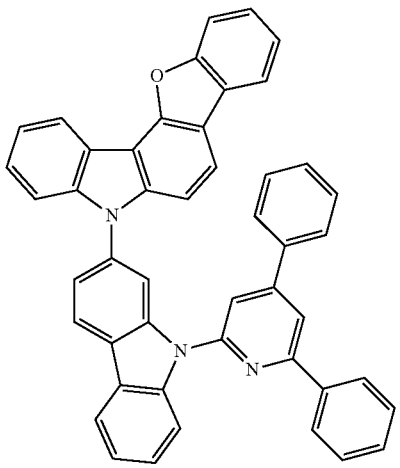

[Chemical Formula B-17]
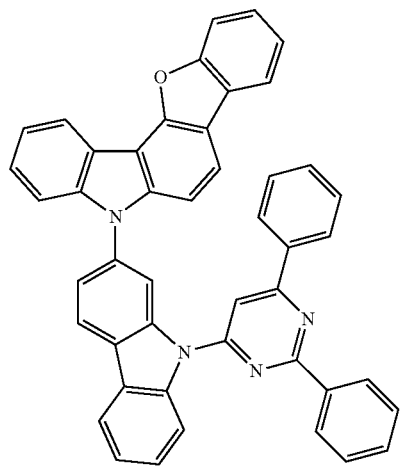
[Chemical Formula B-18]
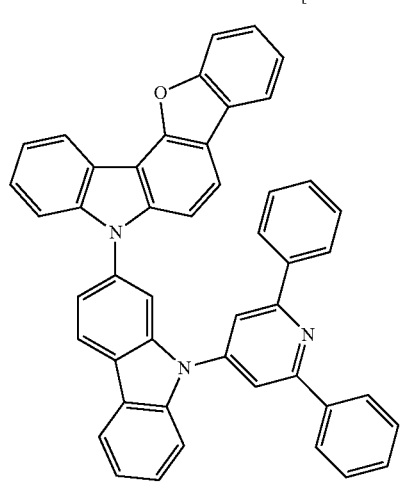
[Chemical Formula C-1]
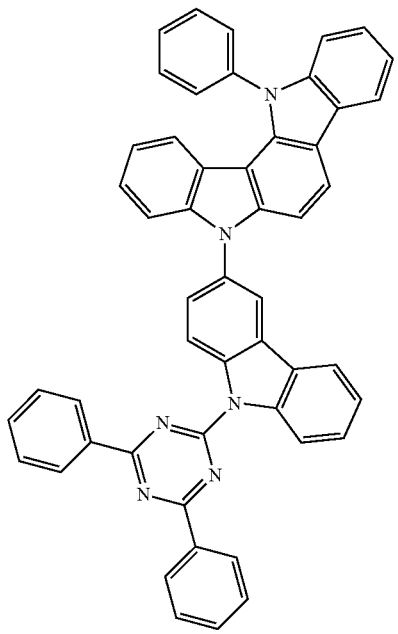
[Chemical Formula C-2]
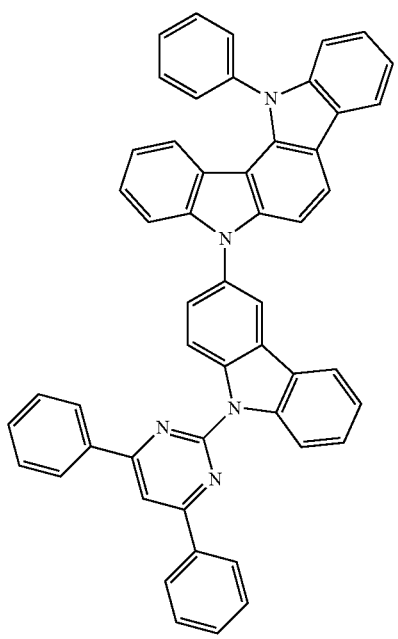
The compound for an organic optoelectronic device may be represented by one of the following Chemical Formulae C-1 to C-18.

[Chemical Formula C-3]
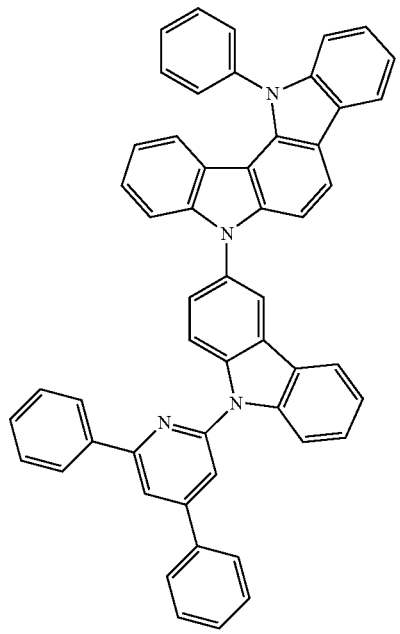
[Chemical Formula C-4]
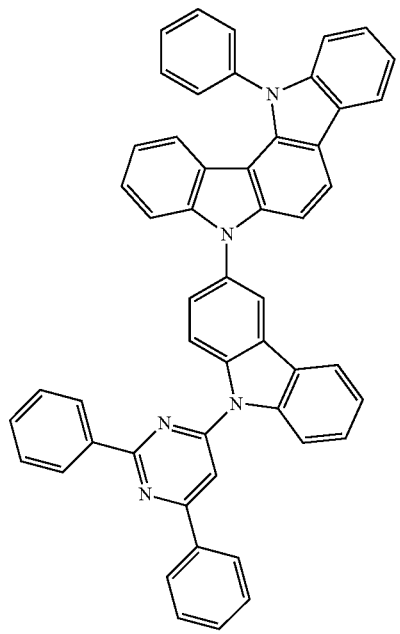
[Chemical Formula C-5]
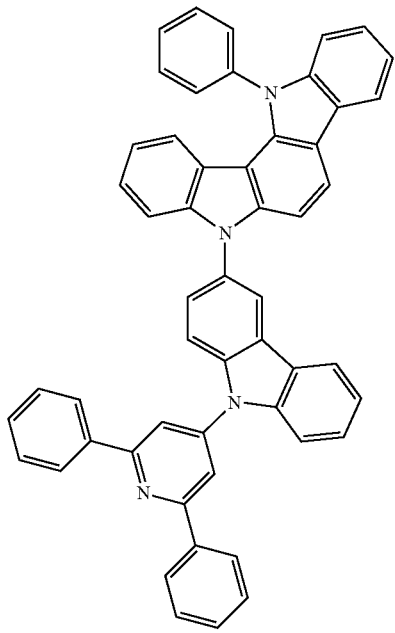
[Chemical Formula C-6]
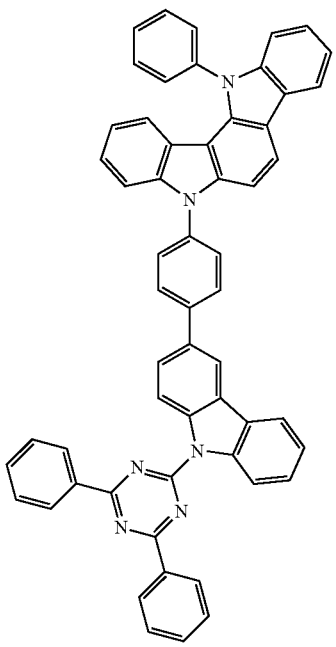

[Chemical Formula C-7]
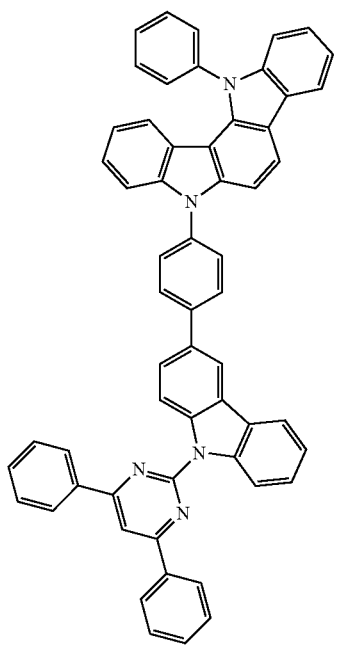
[Chemical Formula C-8]
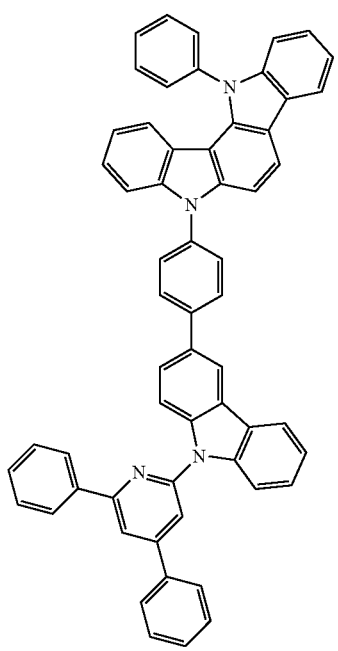
[Chemical Formula C-9]
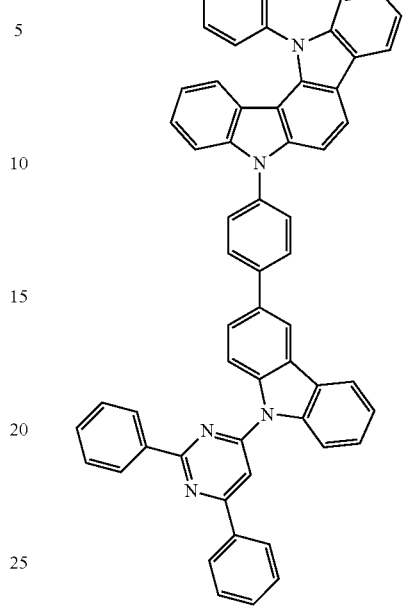
[Chemical Formula C-10]
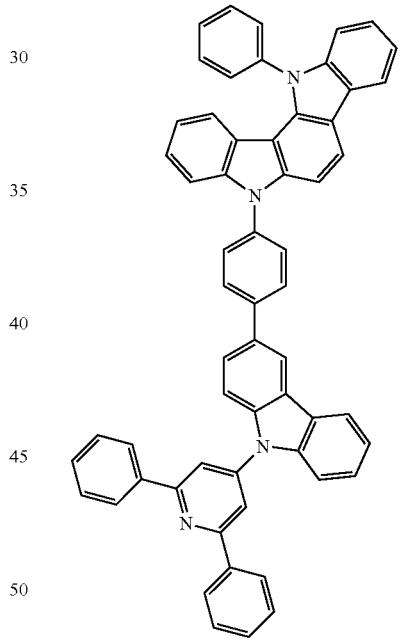
[Chemical Formula C-11]
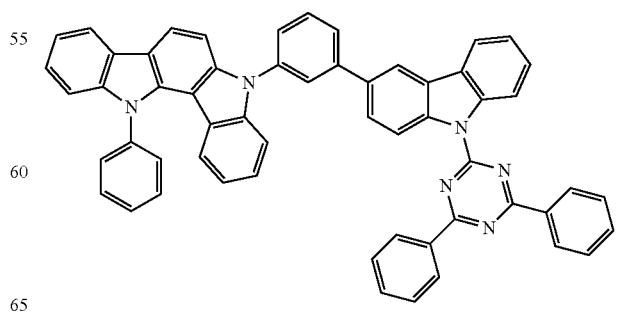

[Chemical Formula C-12]

[Chemical Formula C-13]

[Chemical Formula C-14]

[Chemical Formula C-15]

[Chemical Formula C-16]

[Chemical Formula C-17]

[Chemical Formula C-18]

The compound for an organic optoelectronic device may have triplet exciton energy (T1) of greater than or equal to about 2.0 eV.

The organic optoelectronic device may be selected from an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the above compound for an organic optoelectronic device.

The organic thin layer may be selected from an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the above organic light emitting diode is provided.

Advantageous Effects

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics, and high luminous efficiency at a low driving voltage due to excellent electrochemical and thermal stability.

<Description of Symbols>

Figure 1:
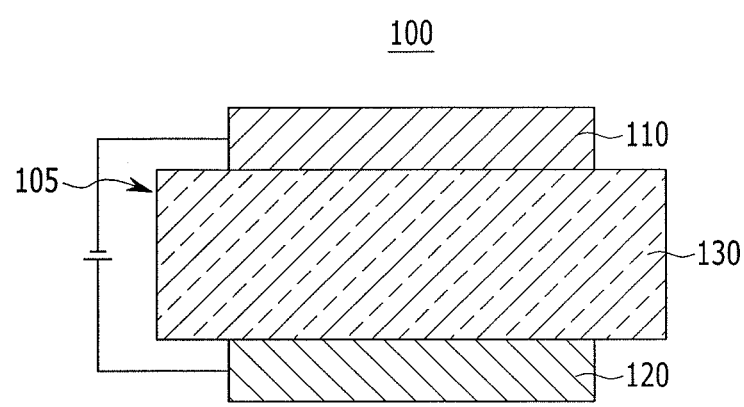
FIGS. 1 to 5 are cross-sectional views showing organic light emitting diodes according to various embodiments of the present invention including the compound for an organic optoelectronic device according to one embodiment of the present invention.

| | |
|---|---|
| 100: organic light emitting diode | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

BEST MODE

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C20 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent selected from the substituted a halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond.

The alkyl group may be "an unsaturated alkyl group" that includes at least one double bond or triple bond.

The "alkenylene group" refers to a functional group of at least one carbon-carbon double bond of at least two carbons, and the "alkynylene group" refers to a functional group of at least one carbon-carbon triple bond of at least two carbons. Regardless of being saturated or unsaturated, the alkyl group may be branched, linear or cyclic.

The alkyl group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl group" includes monocyclic or fused ring polycyclic (i.e., rings sharing adjacent pairs of carbon atoms) groups.

"Heteroaryl group" refers to aryl group including 1 to 3 hetero atoms selected from N, O, S, and P, and remaining carbons. When the heteroaryl group is a fused ring, each ring may include 1 to 3 hetero atoms.

As used herein, the carbazole-based derivative may refer to a substituted structure where a nitrogen atom of a substituted or unsubstituted carbazolyl group is substituted with a hetero atom except nitrogen. Specific examples may be dibenzofuran (a dibenzofuranyl group), dibenzothiophene (a dibenzothiopheneyl group), and the like.

In the present specification, hole characteristics refer to characteristics that holes formed in the anode is easily injected into the emission layer and transported in the emission layer due to conductive characteristics according to HOMO level.

Electron characteristics refer to characteristics that electron formed in the cathode is easily injected into the emission layer and transported in the emission layer due to conductive characteristics according to LUMO level.

A compound for an organic optoelectronic device according to one embodiment of the present invention may have a core structure where a substituent having electron characteristics is bonded with a fused ring including at least one hetero atom.

Since the core structure includes a hetero fused ring having excellent hole characteristics and a substituent having electron characteristics, the compound may be used as a light emitting material, a hole injection material, or a hole transport material for an organic light emitting diode. Specifically, the compound may be appropriate for the light emitting material.

In addition, since the fused ring may decrease symmetry inside the molecule and thus, crystallinity of the compound, the compound may be suppressed from recrystallization inside a device.

At least one substituent combined with the core may be a substituent having electron characteristics.

The compound for an organic optoelectronic device includes a core part and various substituents for a substituent for substituting the core part and thus may have various energy bandgaps.

The compound may have an appropriate energy level depending on the substituents and thus, may bring about excellent effects on efficiency and a driving voltage and also, provides an organic optoelectronic device having excellent electrochemical and thermal stability and thus, improved life-span characteristics during the operation of the organic optoelectronic device.

According to one embodiment of the present invention, the compound for an organic optoelectronic device may be a compound for an organic optoelectronic device represented by a combination of the following Chemical Formula 1; and Chemical Formula 2 or 3.

[Chemical Formula 1]

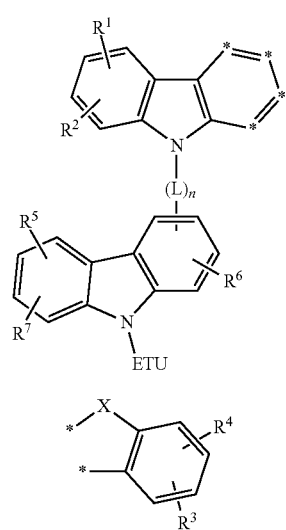

[Chemical Formula 2]

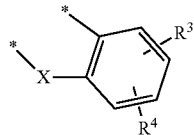

[Chemical Formula 3]

In the above Chemical Formulae 1 to 3, X is —O—, —S—, —NR'—, —SO$_2$—, —P(O)—, or —C(O)—, wherein R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, two *'s of the above Chemical Formula 1 are bonded with the adjacent two *'s of the above Chemical Formula 2 or 3 to form a fused ring, ETU is a substituted or unsubstituted C2 to C30 heteroaryl group having electron characteristics, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

The substituted or unsubstituted C2 to C30 heteroaryl group having electron characteristics may be a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof. But, the substituent is not limited thereto.

A total pi conjugation length (π-conjugation length) is controlled by controlling a length of the L, and thereby a triplet energy bandgap is controlled so as to be very usefully applied to the emission layer of organic optoelectric device as a phosphorescent host. In addition, when a heteroaryl group is introduced, bipolar characteristics are realized in the molecular structure and thus a phosphorescent host having high efficiency may be provided.

The above Chemical Formulae may be appropriately combined to prepare a compound for an organic optoelectronic device having light emission; hole or electron characteristics; film stability; thermal stability; or high triplet exciton energy (T1).

In addition, the above Chemical Formulas may be appropriately combined to prepare a compound having a structure of asymmetric bipolar characteristics, and the structure of asymmetric bipolar characteristics may improve hole/electron-transporting capability and thus, luminous efficiency and performance of a device.

In addition, the above Chemical Formulas may be combined to prepare the compound to have a bulky structure and thus, the bulky structure may decrease crystallinity of the compound. When the compound has lower crystallinity, a device may have a longer life-span.

The compound for an organic optoelectronic device may be represented by the following Chemical Formula 4.

[Chemical Formula 4]

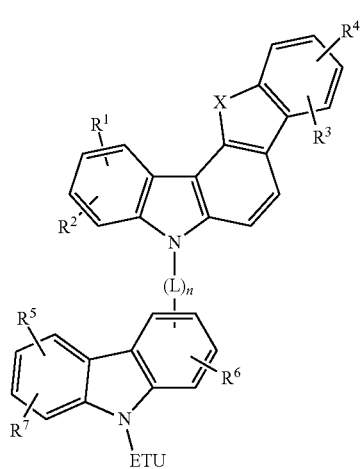

In the above Chemical Formula 4, X is —O—, —S—, —NR'—, —S(O$_2$)—, —P(O)—, or —C(O)—, wherein R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a is substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, ETU is a substituted or unsubstituted C2 to C30 heteroaryl group having electron characteristics, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

A compound having improved thermal stability or oxidation resistance may be provided through a combination of the substituents of the compound.

The compound for an organic optoelectronic device may be represented by the following Chemical Formula 5.

[Chemical Formula 5]

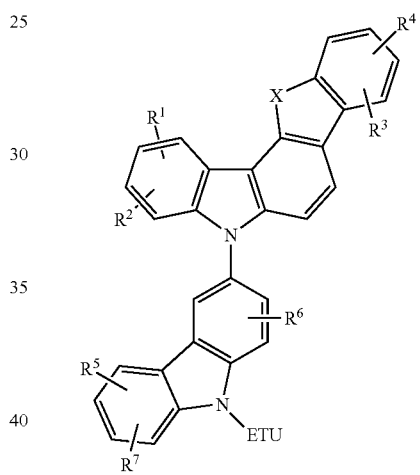

In the above Chemical Formula 5, X is —O—, —S—, —NR'—, —S(O$_2$)—, —P(O)—, or —C(O)—, wherein R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and ETU is a substituted or unsubstituted C2 to C30 heteroaryl group having electron characteristics.

The ETU may be a substituted or unsubstituted pyridinyl group, a substituted or unsubstituted pyrimidinyl group, a substituted or unsubstituted triazinyl group, or a combination thereof.

More specifically, the ETU may be a substituent represented by one of the following Chemical Formulae 6 to 10, but is not limited thereto.

[Chemical Formula 6]

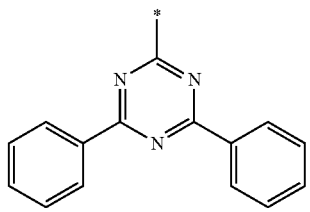

[Chemical Formula 7]

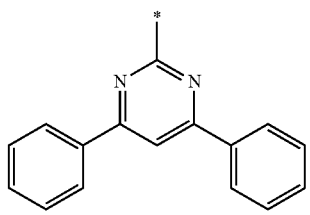

[Chemical Formula 8]

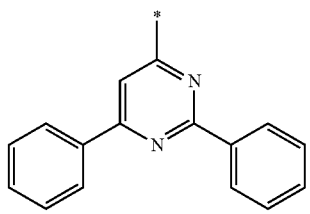

[Chemical Formula 9]

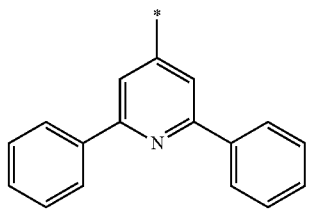

[Chemical Formula 10]

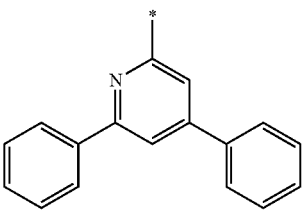

The compound for an organic optoelectronic device according to one embodiment of the present invention may be represented by one of the following Chemical Formulae A-1 to A-18.

[Chemical Formula A-1]

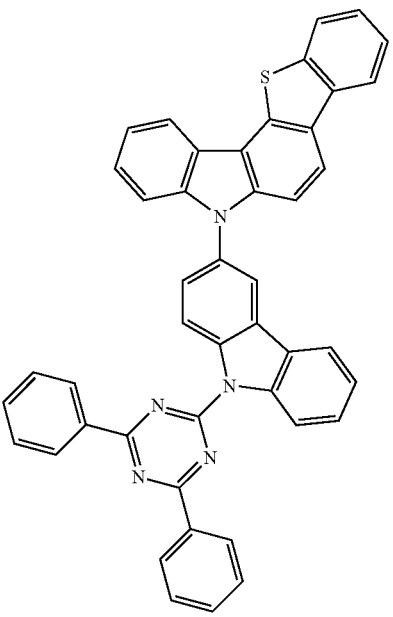

[Chemical Formula A-2]

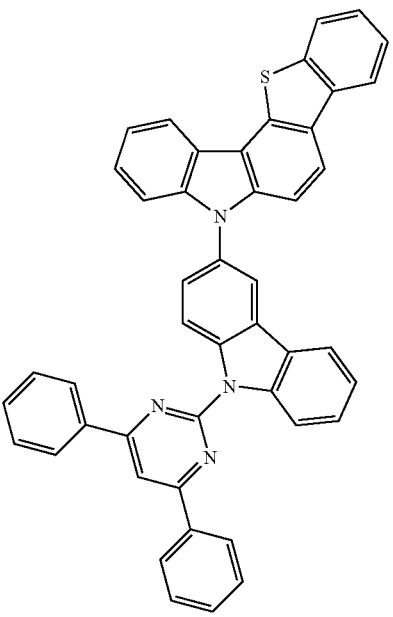

[Chemical Formula A-3]
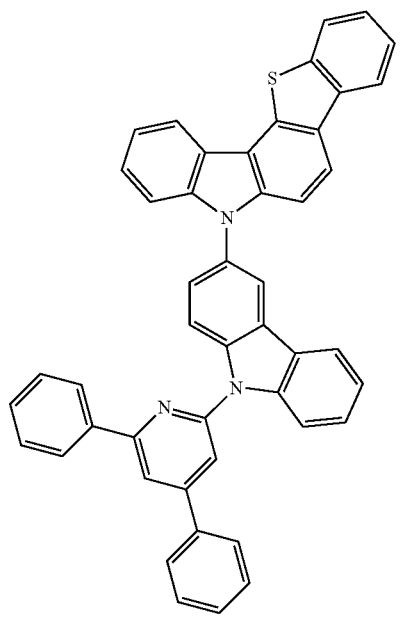
[Chemical Formula A-5]
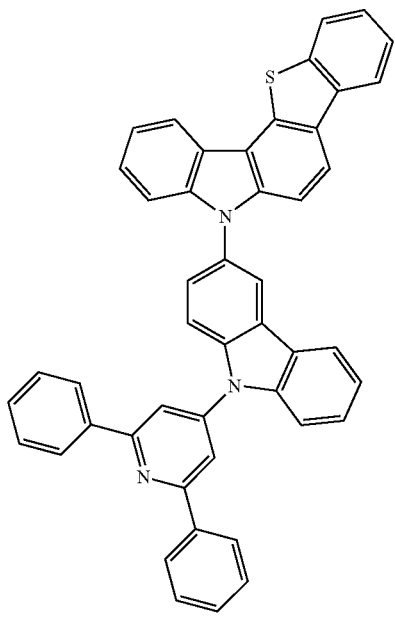
[Chemical Formula A-4]
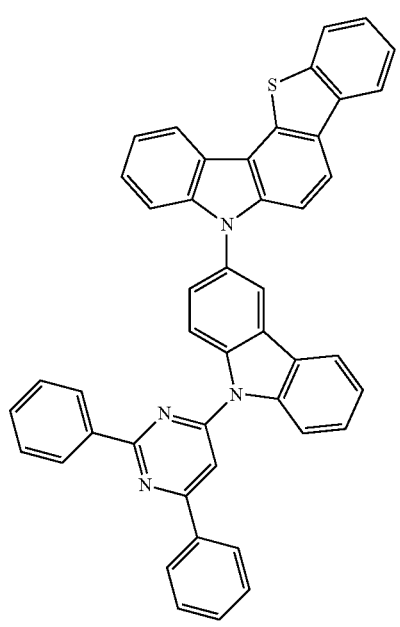
[Chemical Formula A-6]
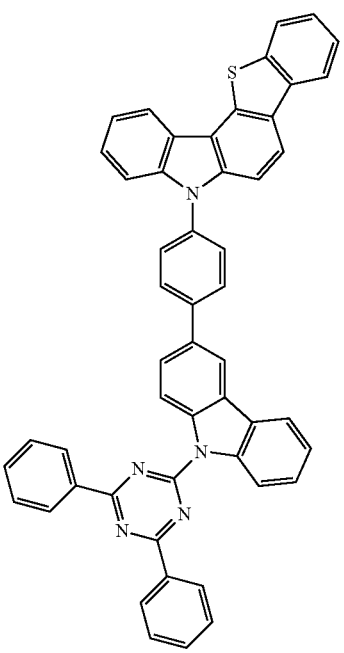

[Chemical Formula A-7]
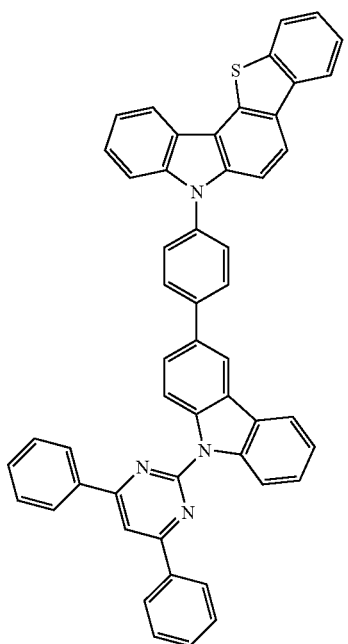
[Chemical Formula A-8]
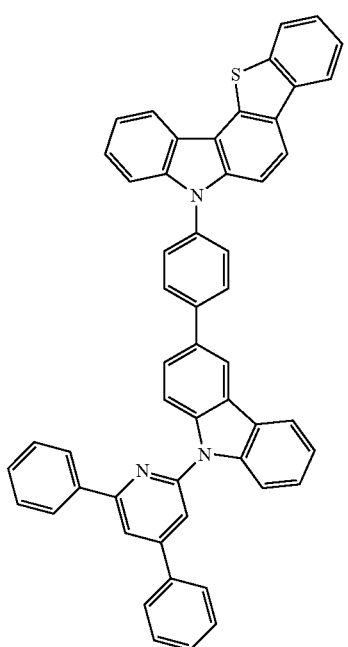
[Chemical Formula A-9]
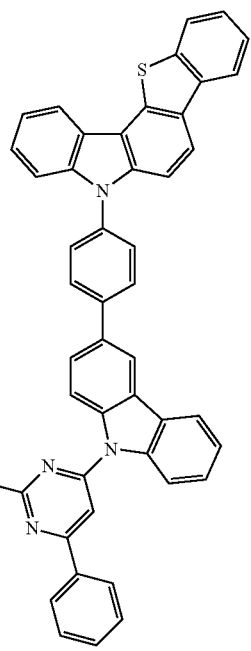
[Chemical Formula A-10]
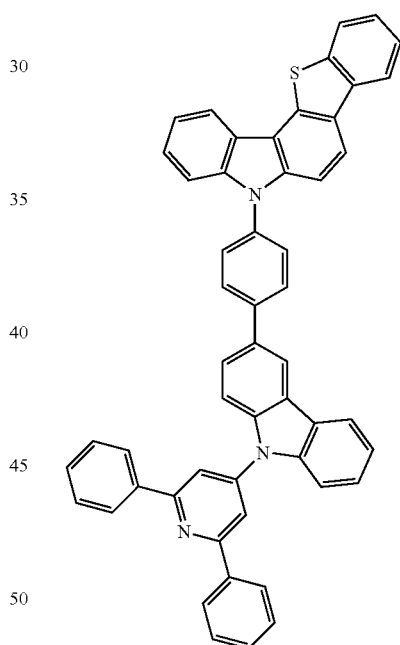
[Chemical Formula A-11]
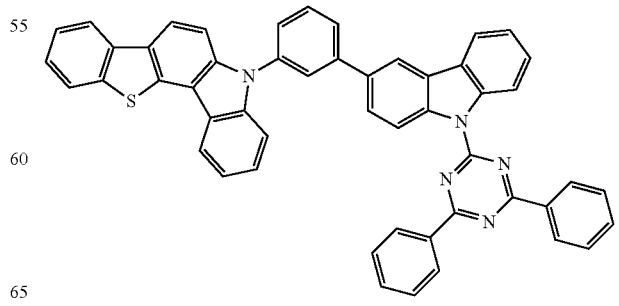

[Chemical Formula A-12]
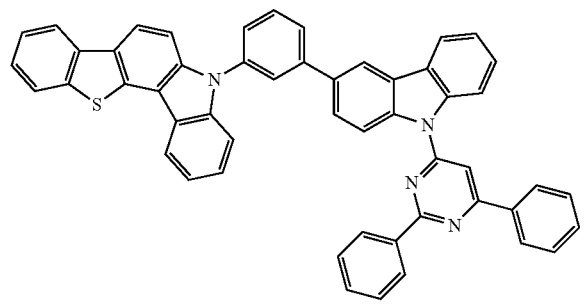
[Chemical Formula A-13]
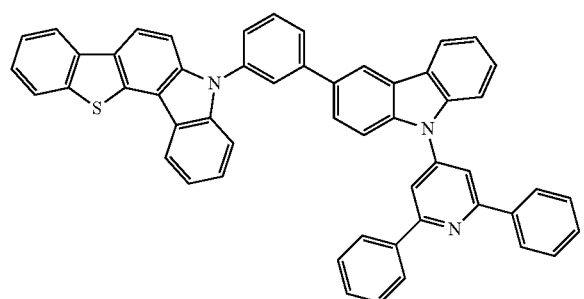
[Chemical Formula A-14]
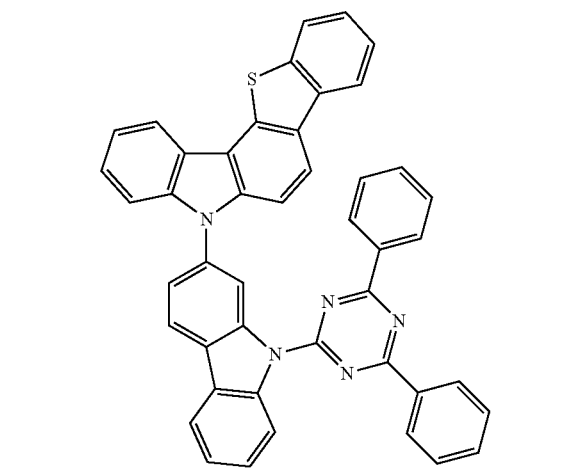
[Chemical Formula A-15]
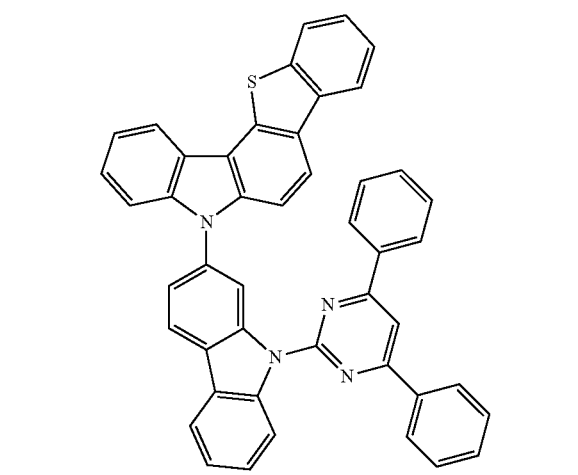
[Chemical Formula A-16]
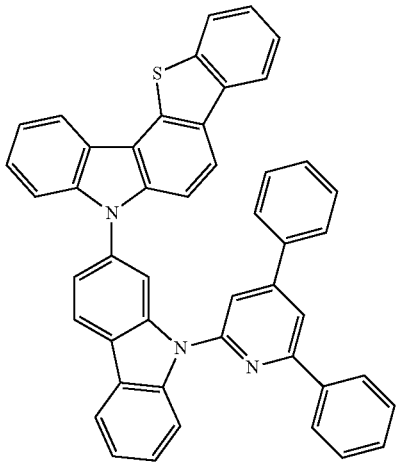
[Chemical Formula A-17]
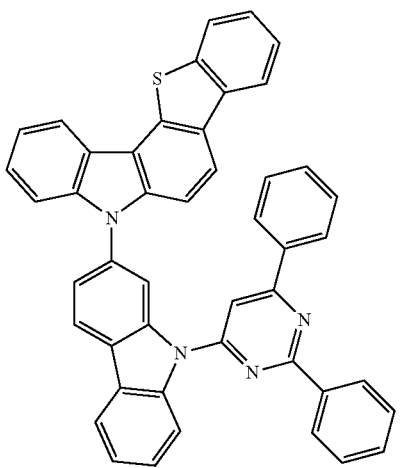
[Chemical Formula A-18]
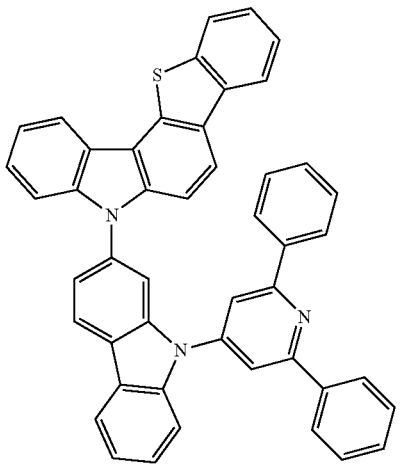
The compound for an organic optoelectronic device according to one embodiment of the present invention may be represented by one of the following Chemical Formulae B-1 to B-18.

[Chemical Formula B-1]
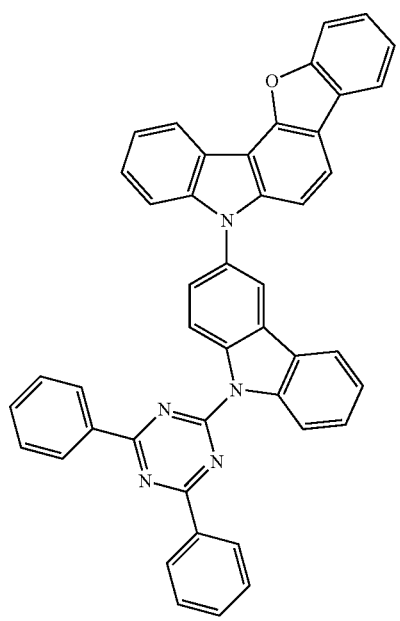
[Chemical Formula B-2]
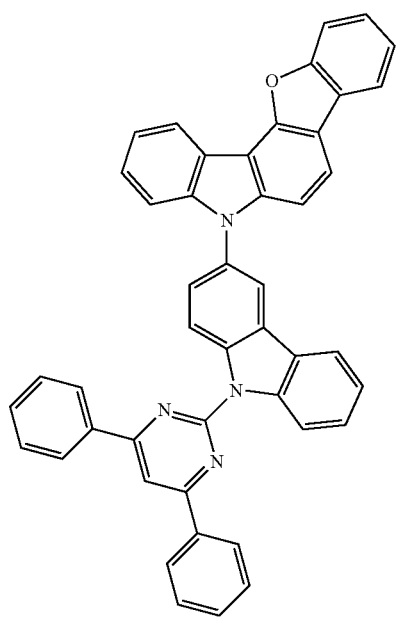
[Chemical Formula B-3]
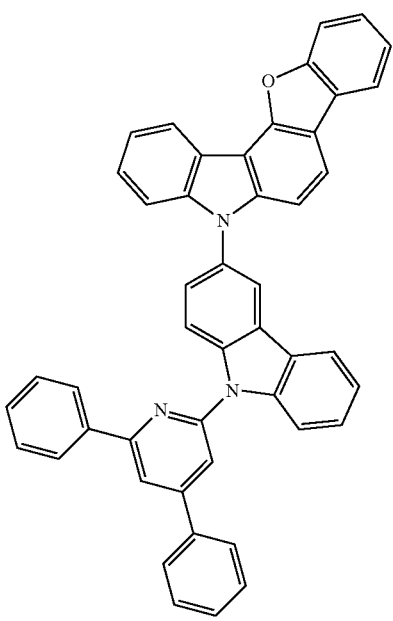
[Chemical Formula B-4]
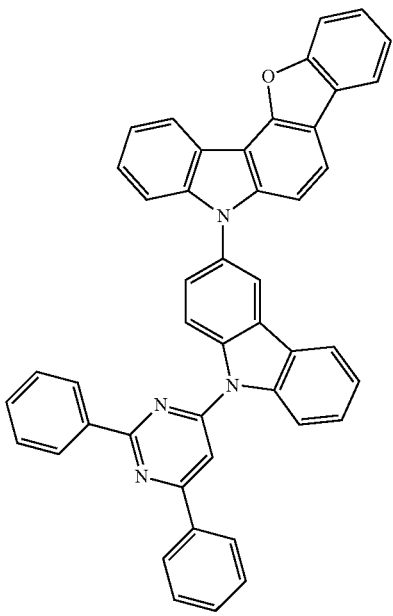

[Chemical Formula B-5]
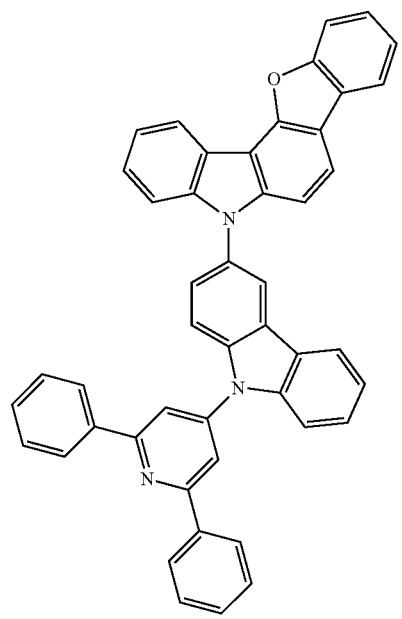
[Chemical Formula B-6]
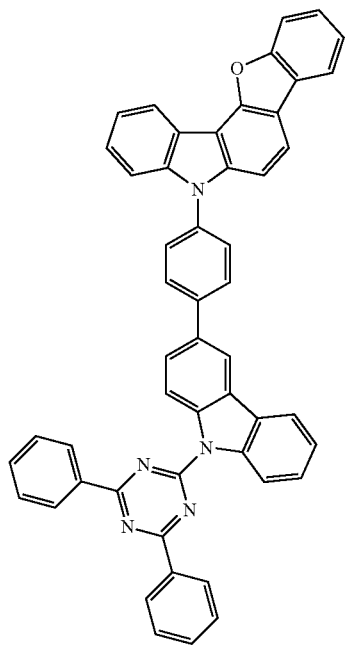
[Chemical Formula B-7]
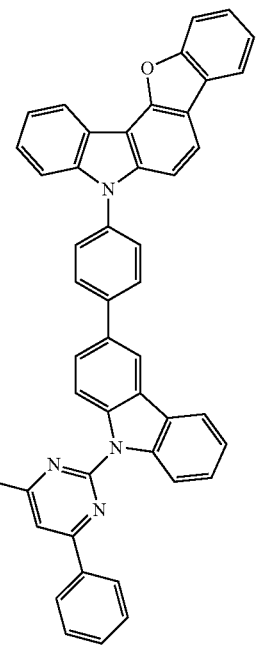
[Chemical Formula B-8]
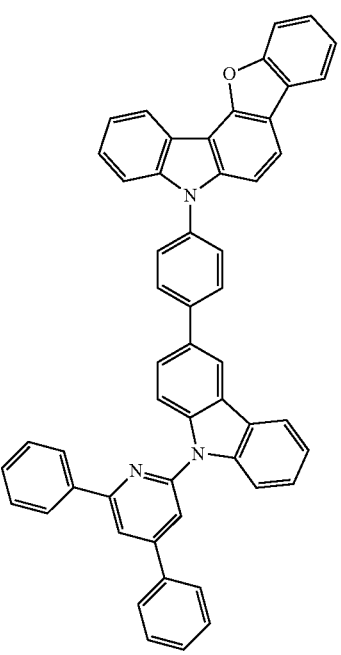

[Chemical Formula B-9]
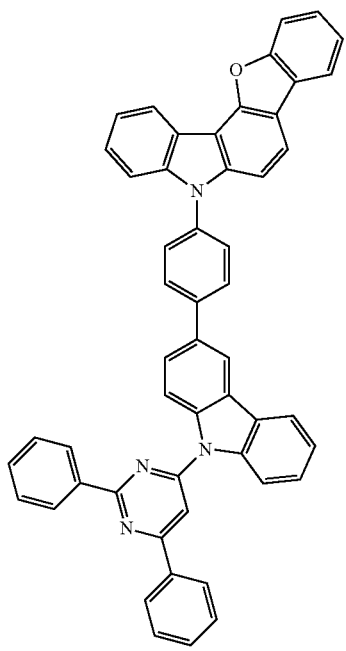
[Chemical Formula B-10]
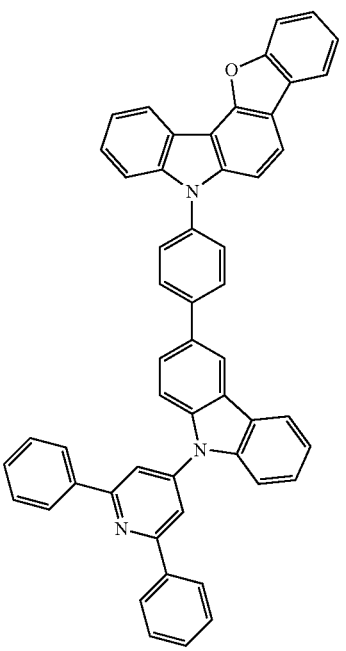
[Chemical Formula B-11]
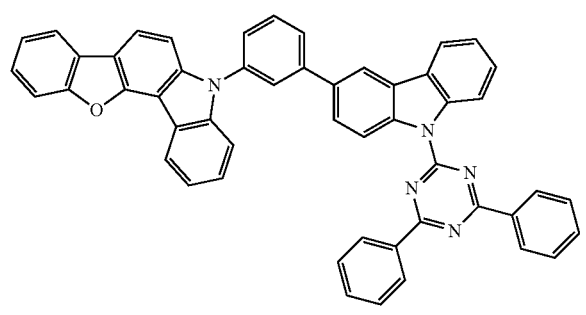
[Chemical Formula B-12]
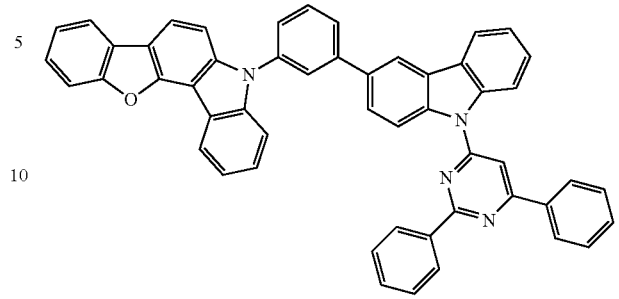
[Chemical Formula B-13]
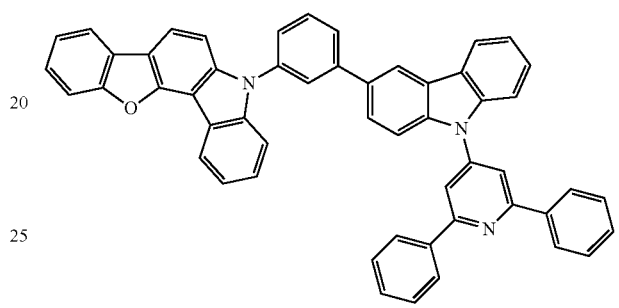
[Chemical Formula B-14]
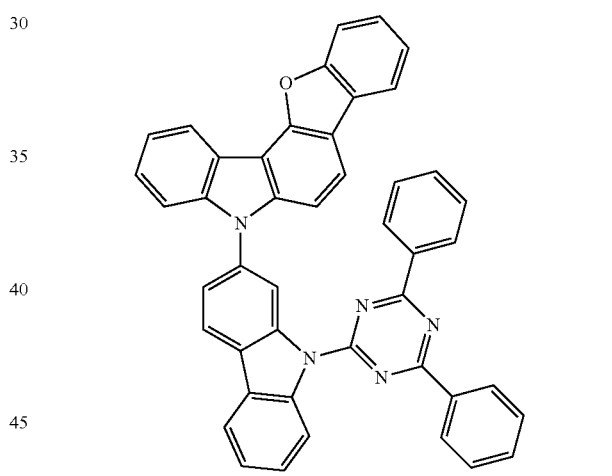
[Chemical Formula B-15]
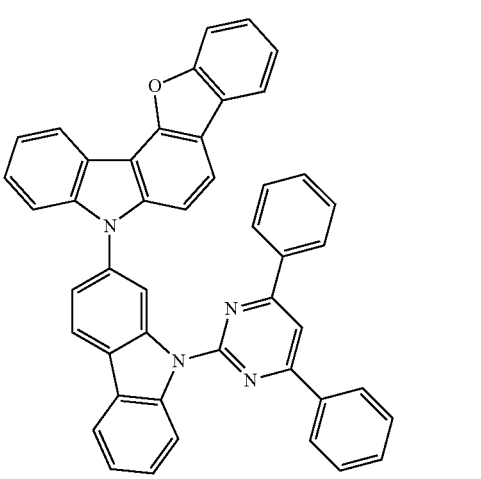

[Chemical Formula B-16]
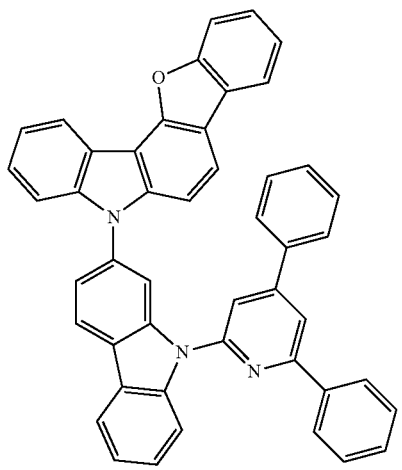
[Chemical Formula B-17]
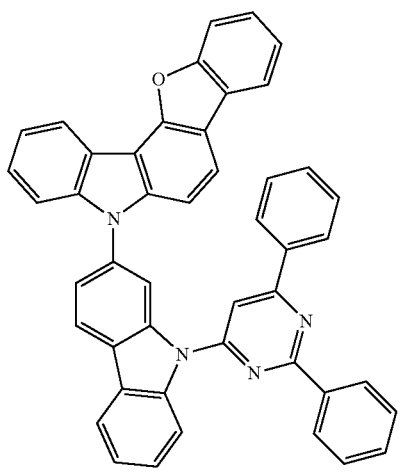
[Chemical Formula B-18]
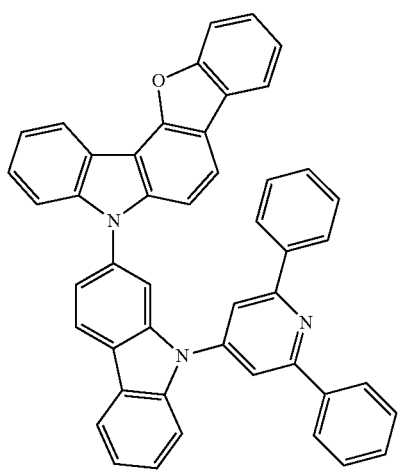
[Chemical Formula C-1]
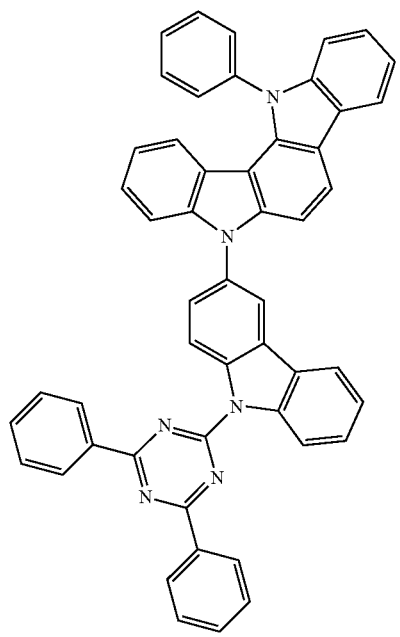
[Chemical Formula C-2]
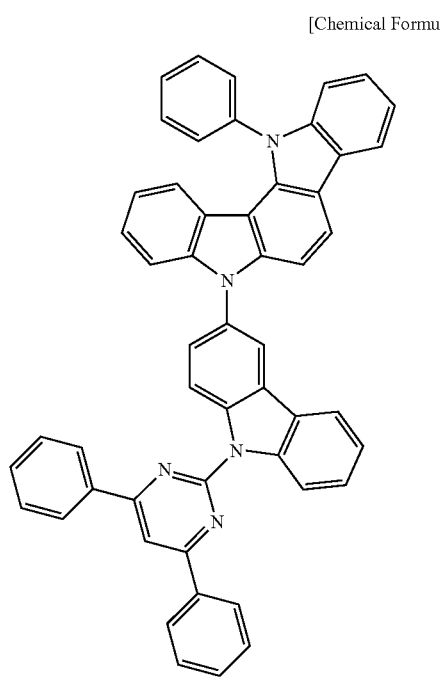
The compound for an organic optoelectronic device according to one embodiment of the present invention may be represented by one of the following Chemical Formulae C-1 to C-18.

[Chemical Formula C-3]
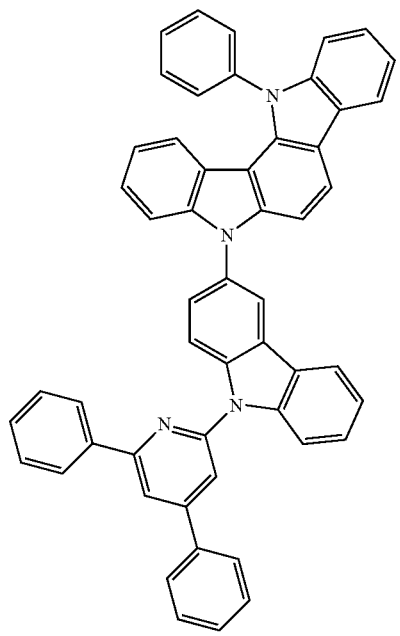
[Chemical Formula C-5]
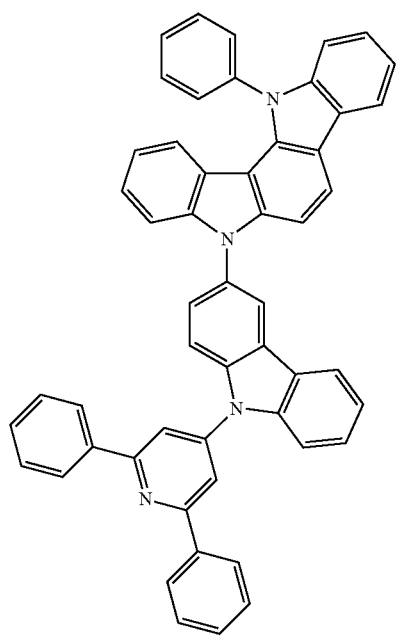
[Chemical Formula C-4]
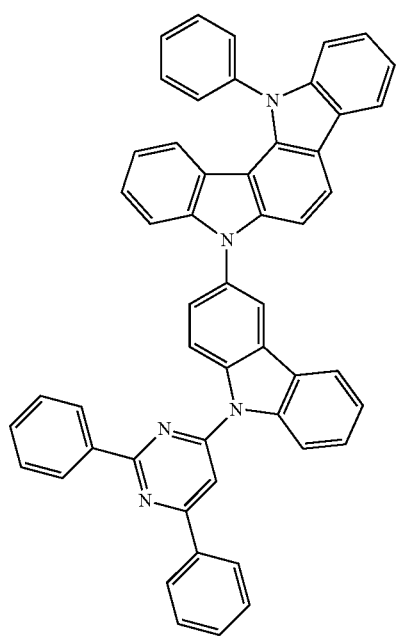
[Chemical Formula C-6]
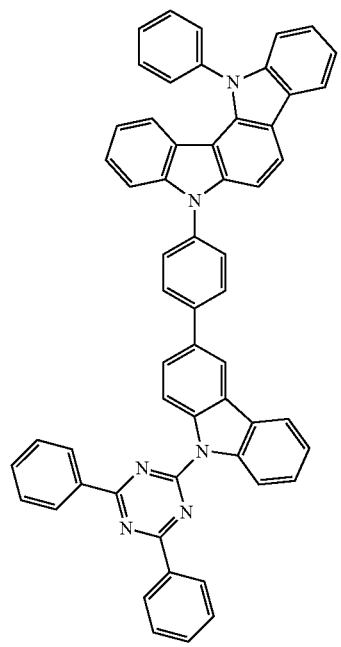

[Chemical Formula C-7]
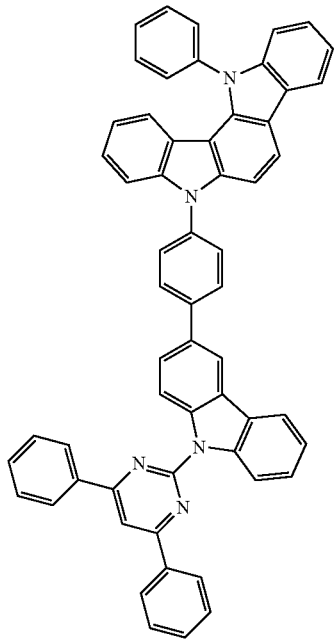
[Chemical Formula C-9]
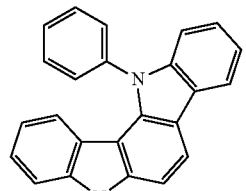
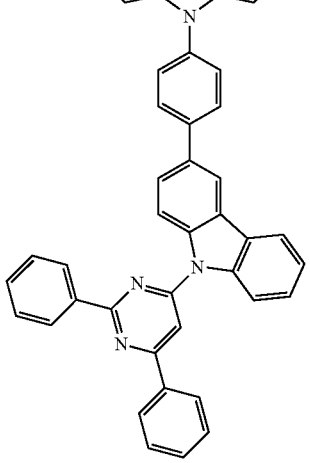
[Chemical Formula C-10]
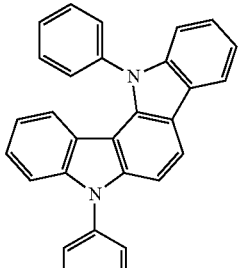
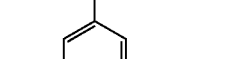
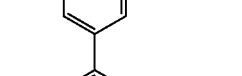
[Chemical Formula C-8]
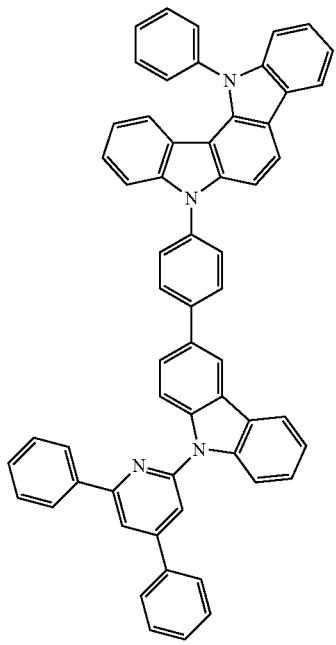
[Chemical Formula C-11]
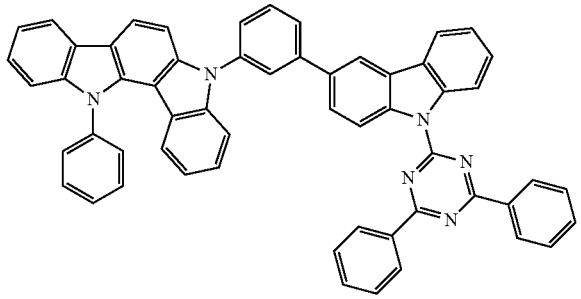

-continued

[Chemical Formula C-12]

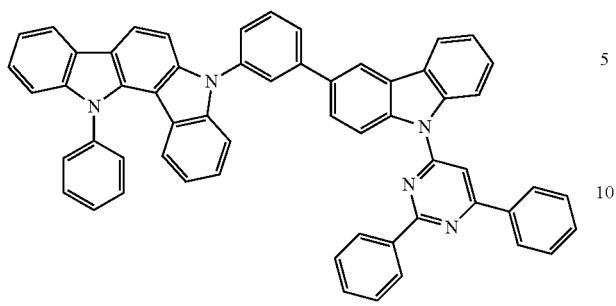

[Chemical Formula C-13]

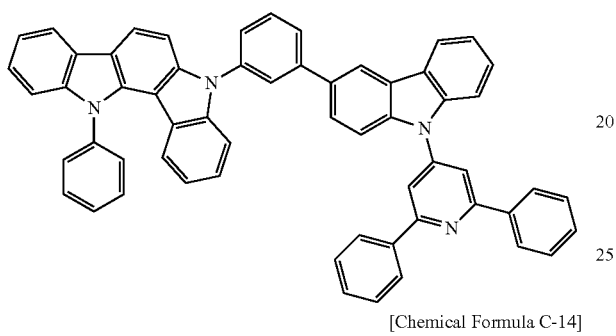

[Chemical Formula C-14]

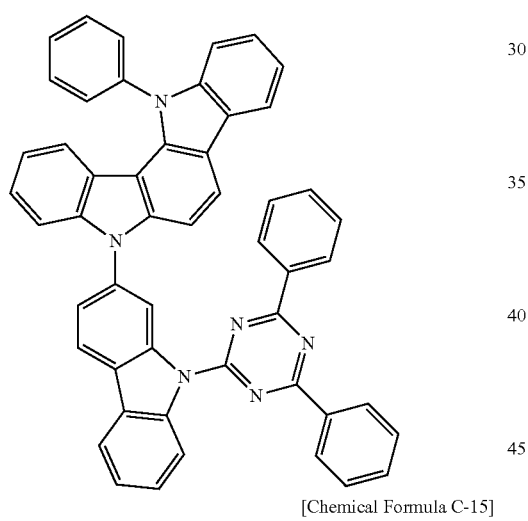

[Chemical Formula C-15]

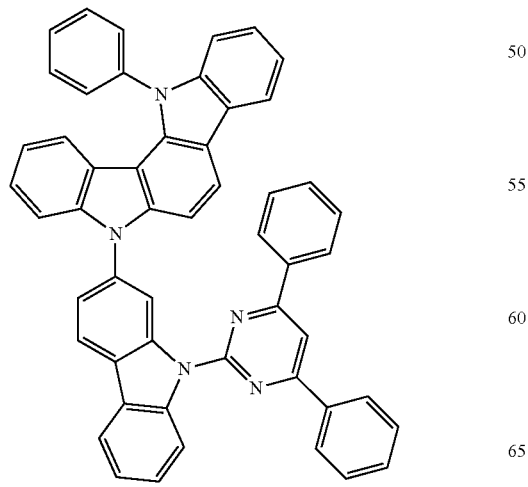

-continued

[Chemical Formula C-16]

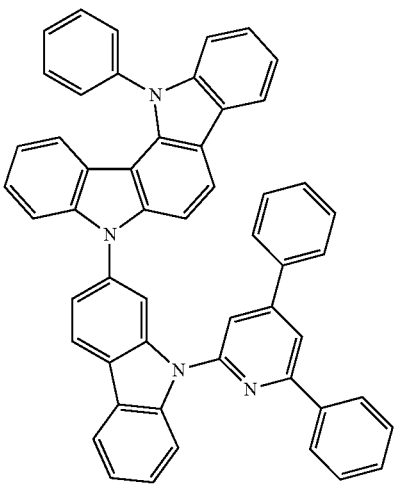

[Chemical Formula C-17]

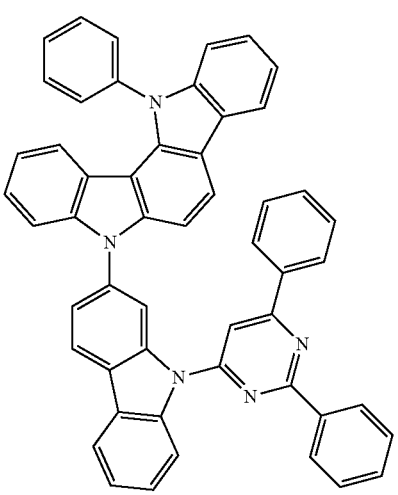

[Chemical Formual C-18]

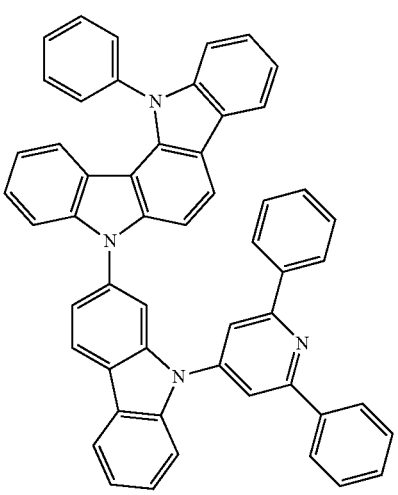

When the above compound according to one embodiment of the present invention requires both electron and hole characteristics, the functional group having electron characteristics may be introduced into the compound to effectively improve life-span of an organic light emitting diode and decrease its driving voltage.

The above compound for an organic optoelectronic device according to one embodiment of the present invention shows a maximum light emitting wavelength in a range of about 320 to about 500 nm, high triplet exciton energy (T1) of greater than equal to about 2.0 eV and specifically, about 2.0 to about 4.0 eV and thus, has an advantage of increasing luminous efficiency of a dopant by well transporting charges of a host having high triplet exciton energy to the dopant and decreasing a driving voltage by freely adjusting HOMO and LUMO energy levels of a material and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from an emission layer, a hole transport layer, a hole injection layer, an electron transport layer, an electron injection layer, a hole blocking layer, and a combination thereof. The at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 5, organic light emitting diodes 100, 200, 300, 400, and 500 according to one embodiment include at least one organic thin layer 105 interposed between an anode 120 and a cathode 110.

The anode 120 includes an anode material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

First, referring to FIG. 1, the organic light emitting diode 100 includes an organic thin layer 105 including only an emission layer 130.

Figure 2:
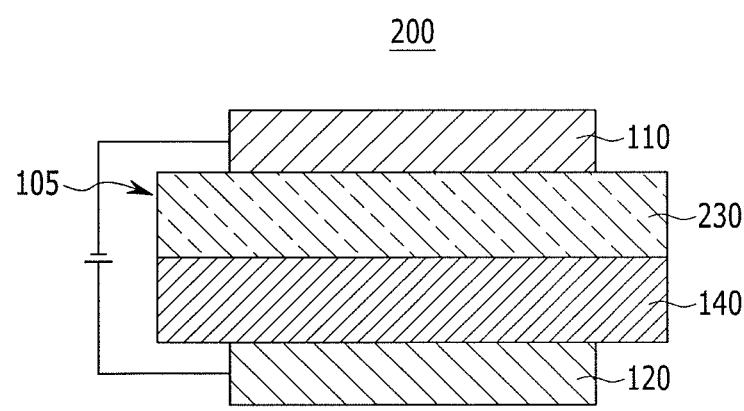

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability.

Figure 3:
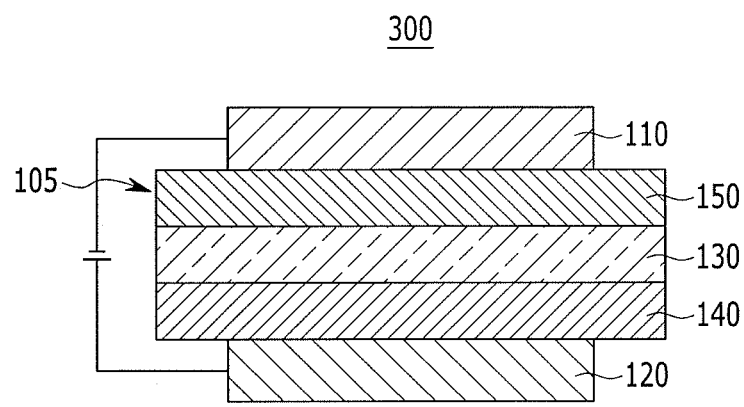

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
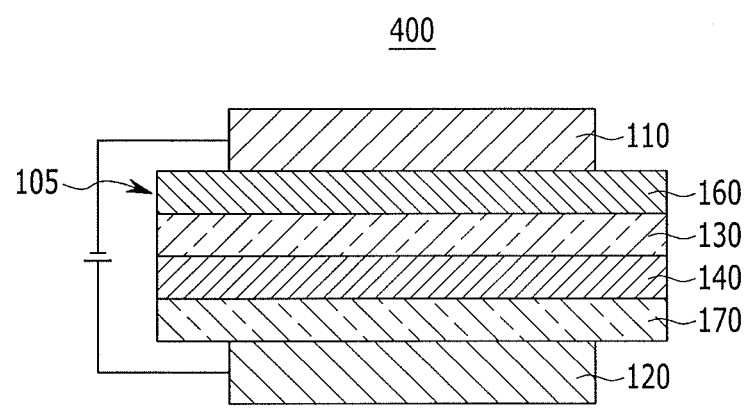

As shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
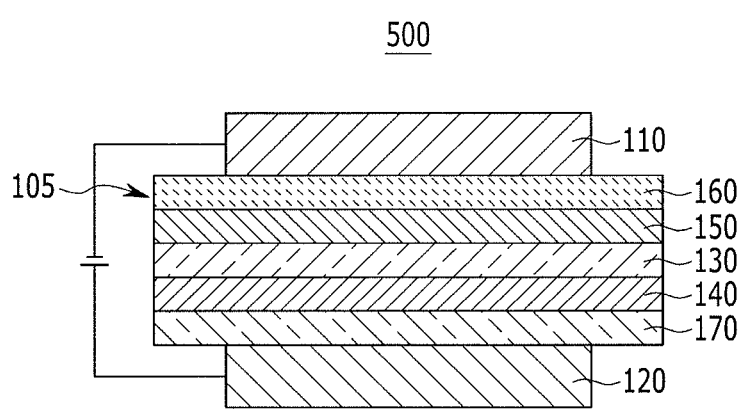

As shown in FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes the compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment of the present invention provides a display device including the light emitting diode according to the above embodiment.

MODE FOR INVENTION

Hereinafter, the embodiments are illustrated in more detail with reference to examples. These examples, however, should not in any sense be interpreted as limiting the scope of the present invention.

Preparation of Compound for Organic Optoelectronic Device

Example 1: Preparation of Compound A-1

[Reaction Scheme 1]

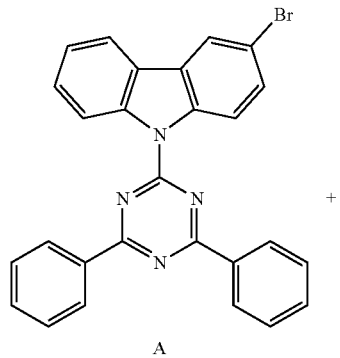

A

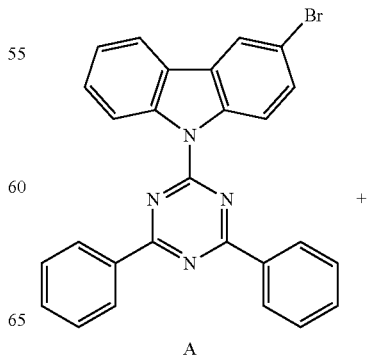

A-1

23.0 g of a compound A and 14.5 g of a compound B were dissolved in 350 mL of toluene under a 1 L round-bottomed flask equipped with a thermometer, a reflux condenser, and an agitator under a nitrogen atmosphere, 13.3 g of sodium tert-butoxide (NaOtBu), 2.8 g of palladium dibenzylideneamine (Pd(0)dba$_2$), and 2.0 g of tertiarybutyl phosphorus (a 50% solution in toluene) were added thereto, and the mixture was refluxed for 12 hours in a reactor. The resultant was naturally cooling down to room temperature and precipitated in 1.2 L of methanol and then, agitated for 1 hour. A solid produced therein was filtered and added to 1.2 L of water to prepare slurry, and the slurry was agitated for one hour and then, filtered again. The filtered solid was dried and then, dissolved in 1 L of monochlorobenzene by heating, and the solution was passed through a celite/silica pad. The passed solution was heated and concentrated down to 500 mL and then, naturally cooled down to room temperature. A solid produced therein was filtered and washed with 300 mL of acetone. The solid was dried at 70° C. for 12 hours under vacuum, obtaining 24.7 g of a compound A-1 (a synthesis yield: 74%).

Example 2: Preparation of Compound B-1

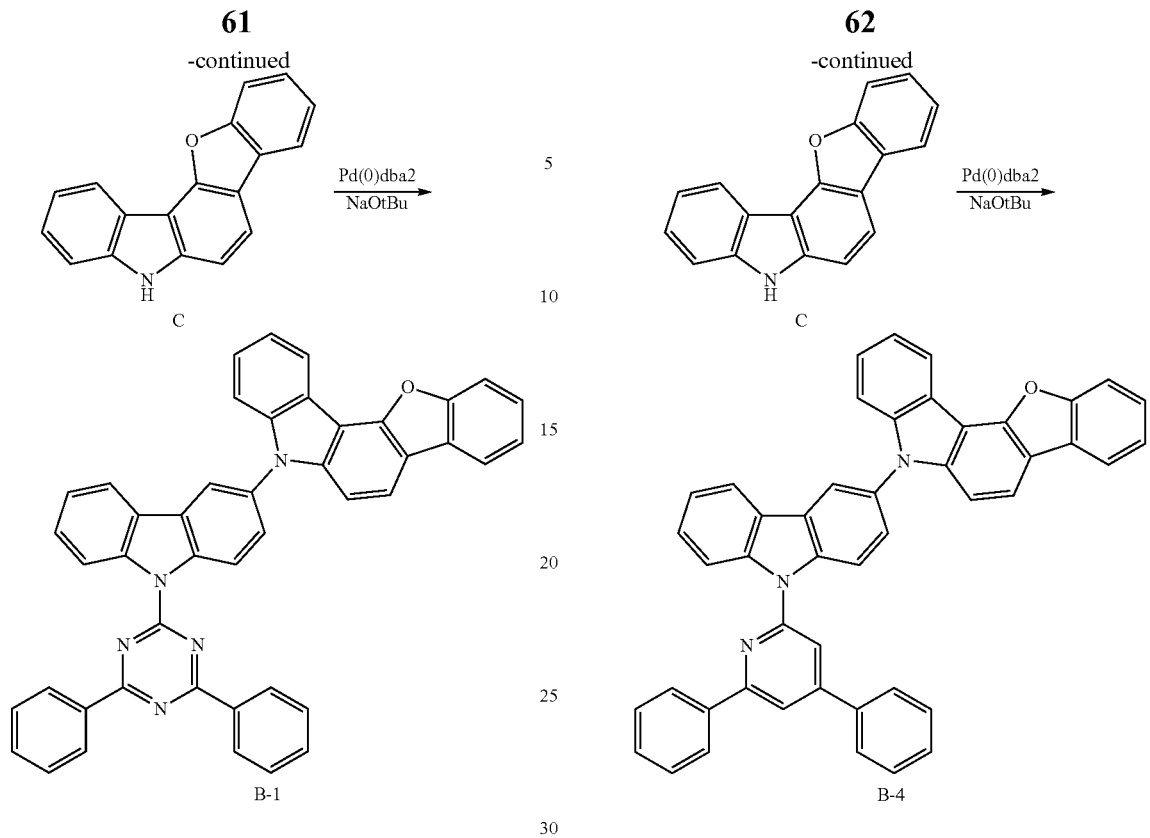

23.0 g of a compound A and 13.6 g of a compound C was dissolved in 350 mL of toluene in a 1 L round-bottomed flask equipped with a thermometer, a reflux condenser, and an agitator under a nitrogen atmosphere, 13.3 g of sodium tert-butoxide (NaOtBu), 2.8 g of palladium dibenzylideneamine (Pd(0)dba$_2$), and 2.0 g of tertiarybutyl phosphorus (a 50% solution in toluene), and the mixture was refluxed for 12 hours in a reactor. The resultant was naturally cooled down to room temperature and precipitated in 1.2 L of methanol and then, agitated for one hour. A solid produced therein was filtered and added to 1.2 L of water to prepare slurry, and the slurry was agitated for one hour and refiltered. The filtered solid was dried and dissolved in 1 L of monochlorobenzene by heating, and then, the solution was passed through a celite/silica pad. The passed solution was heated and concentrated down to 500 mL and then, naturally cooled down to room temperature. A solid produced therein was filtered and washed with 300 mL of acetone. The solid was dried at 70° C. for 12 hours under vacuum, obtaining 26.2 g of a compound B-1 (a synthesis yield: 80%).

Example 3: Preparation of Compound B-4

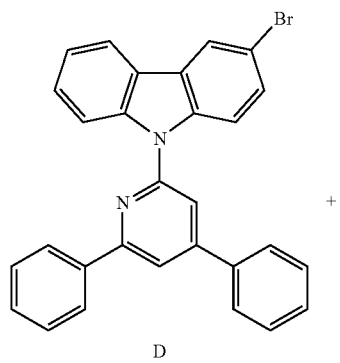

22.9 g of a compound D and 13.6 g of a compound C were dissolved in 0.350 mL of toluene in a 1 L round-bottomed flask equipped with a thermometer, a reflux condenser, and an agitator under a nitrogen atmosphere, 13.3 g of sodium tert-butoxide (NaOtBu), 2.8 g of palladium dibenzylideneamine (Pd(0)dba$_2$), and 2.0 g of tertiarybutyl phosphorus (a 50% solution in toluene) were added thereto, and the mixture was refluxed in a reactor for 12 hours. The resultant was naturally cooled down to room temperature and precipitated in 1.2 L of methanol and then, agitated for one hour. A solid produced therein was filtered and added to 1.2 L of water to prepare slurry, and the slurry was agitated for 1 hour and filtered again. The filtered solid was dried and heated and dissolved in 1 L of monochlorobenzene, and the solution was passed through a celite/silica pad. The passed solution was heated and concentrated down to 500 mL and then, naturally cooled down to room temperature. A solid produced therein was filtered and washed with 300 mL of acetone. The solid was dried at 70° C. for 12 hours under vacuum, obtaining 22.8 g of a compound B-4 (a synthesis yield: 70%).

Manufacture of Organic Light Emitting Diode

Example 4: Manufacture of Organic Photoelectric Device

A glass substrate coated with a 1500 Å-thick ITO (indium tin oxide) thin film was washed with distilled water ultrasonic wave. When the washing with distilled water was complete, the glass substrate was ultrasonic wave-washed with a solvent such as isopropyl alcohol, acetone, methanol, and the like and dried, then, moved to a plasma cleaner, cleaned by using oxygen plasma for 5 minutes there, and moved to a vacuum depositor. This ITO transparent electrode was used as an anode, and a 1200 Å-thick hole injection layer (HIL) was formed by vacuum-depositing the following HTM compound on the ITO substrate.

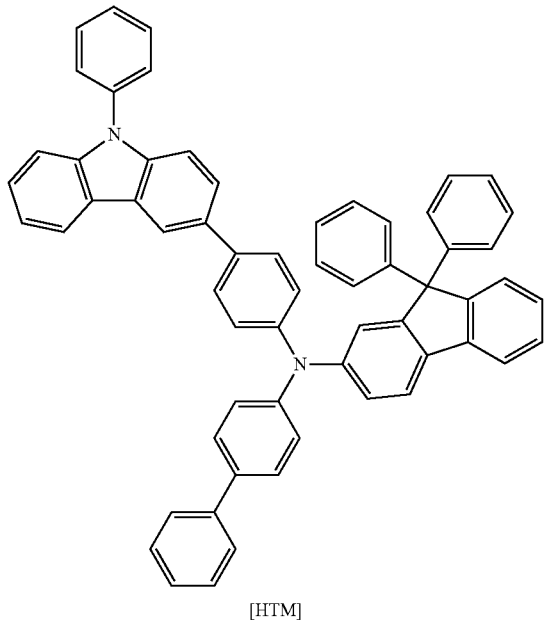

[HTM]

On the hole transport layer (HTL), a 300 Å-thick emission layer was formed by using the synthesized material A-1 of Example 1 as a host, doping it with 7 wt % of the following PhGD compound as a phosphorescence green dopant, and vacuum-depositing the doped host.

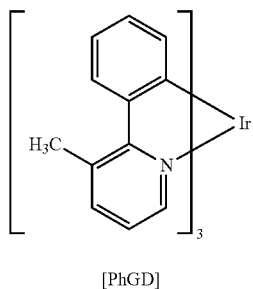

[PhGD]

Subsequently, an electron transport layer (ETL) was formed on the emission layer by laminating the following BAlq [bis(2-methyl-8-quinolinolato-N1,O8)-(1,1'-biphenyl-4-olato)aluminum] compound to 50 Å thick and sequentially, the following Alq3 [tris(8-hydroxyquinolinato)aluminum] compound to be 250 Å thick. On the electron transport layer (ETL), a cathode was formed by sequentially vacuum-depositing LiF to be 5 Å thick and Al to be 1000 Å thick, manufacturing an organic light emitting diode.

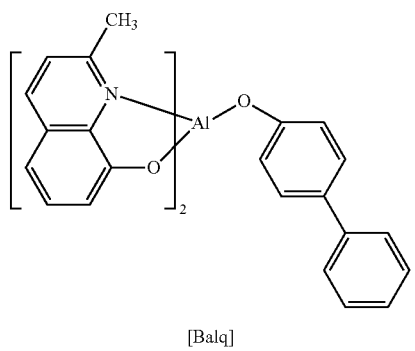

[Balq]

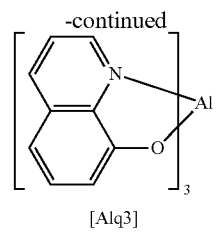

[Alq3]

Example 5

An organic light emitting diode was manufactured according to the same method as Example 4 except for using the synthesized B-1 of Example 2 instead of the compound of Example 1.

Example 6

An organic light emitting diode was manufactured according to the same method as Example 4 except for using the synthesized B-4 of Example 3 instead of the compound of Example 1.

Comparative Example 1

An organic light emitting diode was manufactured according to the same method as Example 4 except for using the following compound of CT [3,6-diphenyl-9-(4,6-diphenyl-1,3,5-triazin-2-yl)-9H-carbazole] as a host instead of the compound of Example 1.

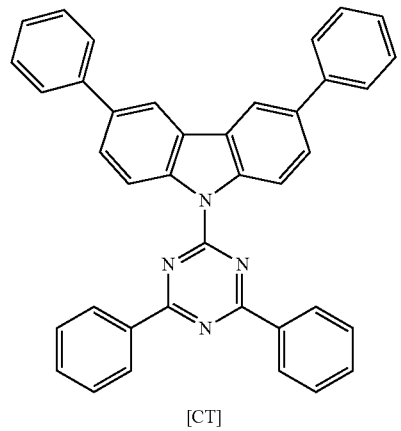

[CT]

(Performance Measurement of Organic Light Emitting Diode)

Current density change, luminance change, and luminous efficiency of each organic light emitting diode according to Examples 4 to 6 and Comparative Example 1 depending on a voltage were measured.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0V to 10 V.

(3) Measurement of Luminous Efficiency

The luminance, current density, and voltage obtained from the (1) and (2) were used to calculate current efficiency (cd/A) at the same current density (10 mA/cm$^2$).

(4) Measurement of Life-Span

The life-span was measured at initial luminance 3500 cd/m$^2$.

The evaluation results are provided in the following Table 1.

TABLE 1

|  | Host | Vd | Cd/A | cd/m$^2$ | CIEx | CIEy | Life-span (h) |
|---|---|---|---|---|---|---|---|
| Comparative Example 1 | CT | 3.3 | 42.2 | 3500 | 0.350 | 0.620 | 25 |
| Example 4 | A-1 | 4.1 | 42.4 | 3500 | 0.353 | 0.613 | 88 |
| Example 5 | B-1 | 3.8 | 57.6 | 3500 | 0.347 | 0.618 | >150 |
| Example 6 | B-4 | 4.4 | 55.8 | 3500 | 0.344 | 0.620 | 52 |

Figure 6:
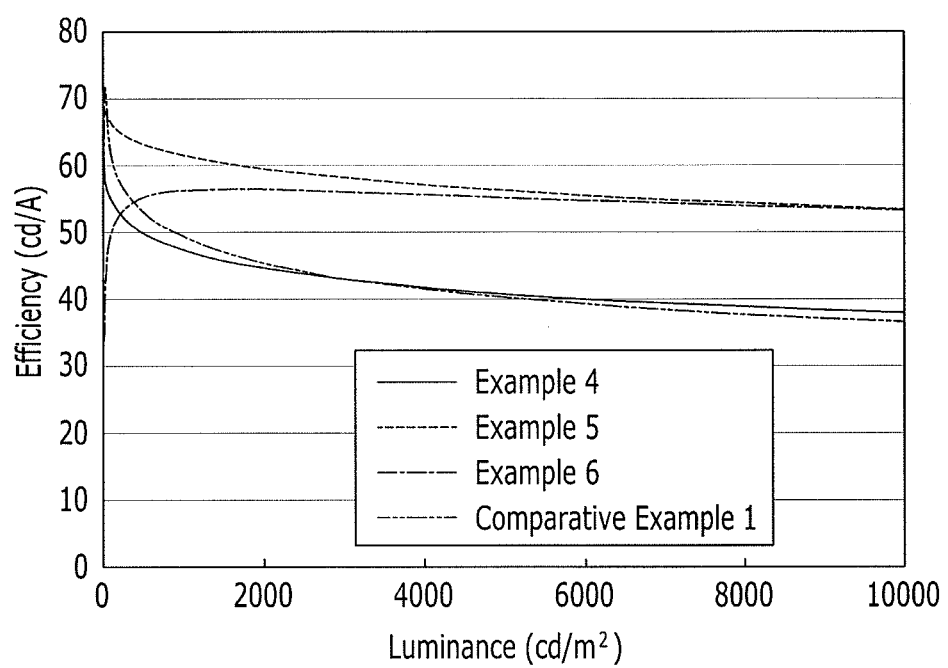
FIG. 6 shows a luminous efficiency data depending on luminance of a device.

FIG. 6 shows a luminous efficiency data depending on luminance of a device.

Figure 7:
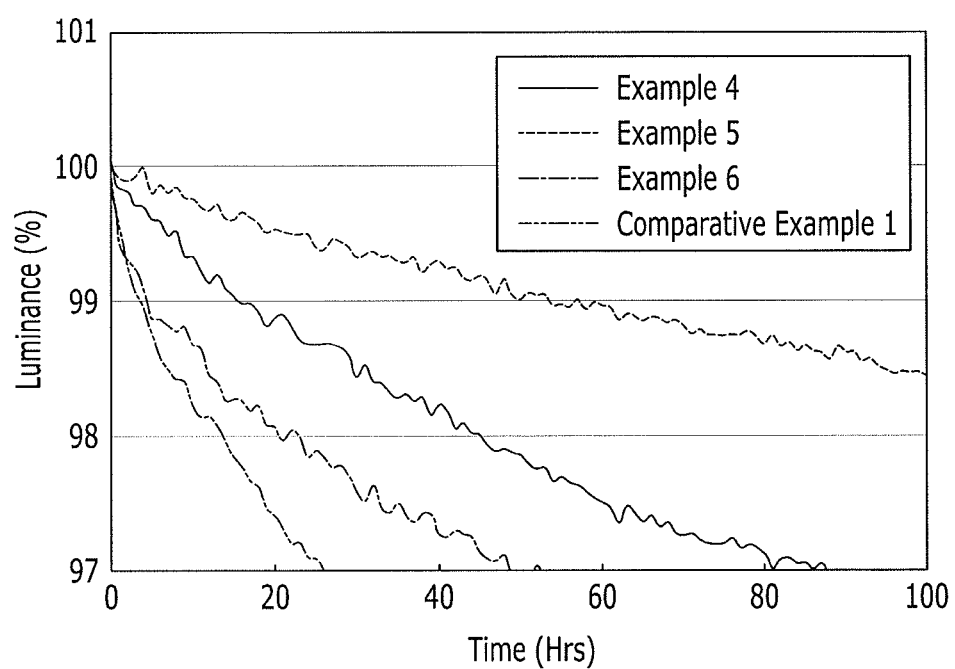
FIG. 7 is a curved line data of a life-span of a device.

FIG. 7 is a curved line data of a life-span of a device.

As shown in Table 1 and FIGS. 6 and 7, efficiency and life-span of the organic light emitting diodes using Examples 4 to 6 as a host were improved compared with the organic light emitting diode using Comparative Example 1 as a host for an emission layer.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. An organic light emitting diode, comprising:
    an anode, a cathode and at least one organic thin layer interposed between the anode and cathode, the organic thin layer including an emission layer,
    wherein the emission layer includes a compound for an organic optoelectronic device represented by a combination of the following Chemical Formula 1; and Chemical Formula 2 or 3, and a phosphorescence dopant, the compound for an organic optoelectronic device having triplet exciton energy (T1) of greater than or equal to about 2.0 eV, provided that the compound for an organic optoelectronic device is not a compound represented by the following Chemical Formula B-5:

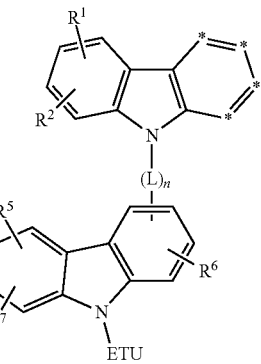

[Chemical Formula 1]

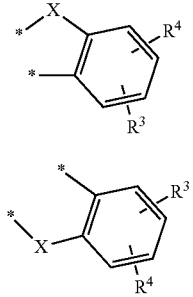

[Chemical Formula 2]

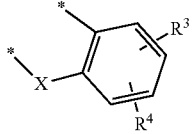

[Chemical Formula 3]

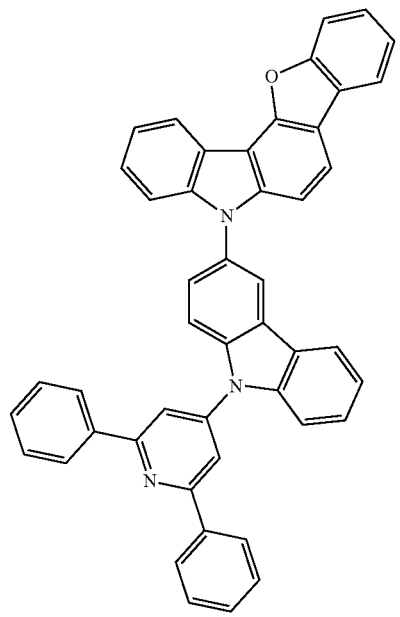

[Chemical Formula B-5]

wherein, in the above Chemical Formulae 1 to 3,
X is —O— or —S—,
R' and R$^1$ to R$^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, two *'s of the above Chemical Formula 1 are bonded with the adjacent two *'s of the above Chemical Formula 2 or 3 to form a fused ring, when X is S, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, when X is O, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, L is a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

2. The organic light emitting diode of claim 1, wherein the compound for an organic optoelectronic device is represented by the following Chemical Formula 4:

[Chemical Formula 4]

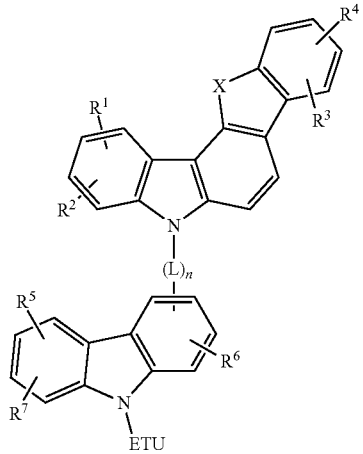

wherein, in the above Chemical Formula 4,

X is —O— or —S—,

R' and R¹ to R⁷ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, when X is S, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, when X is O, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, L is a single bond, a substituted or unsubstituted C2 to C6 alkynylene group, a substituted or unsubstituted C2 to C6 alkynylene group, a substituted or unsubstituted C6 to C30 arylene group, a substituted or unsubstituted C3 to C30 heteroarylene group, or a combination thereof, and n is 0 or 1.

3. The organic light emitting diode of claim 1, wherein the compound for an organic optoelectronic device is represented by the following Chemical Formula 5:

[Chemical Formula 5]

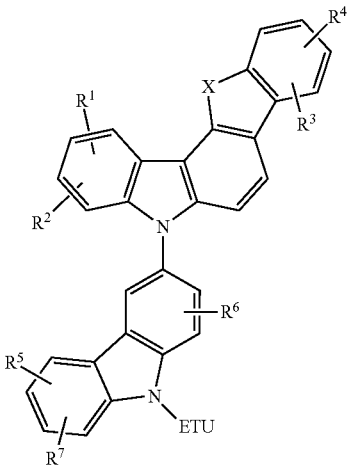

wherein, in the above Chemical Formula 5,

X is —O— or —S—,

R' and $R^1$ to $R^7$ are the same or different and independently hydrogen, deuterium, a halogen, a cyano group, a hydroxy group, an amino group, a substituted or unsubstituted C1 to C20 amine group, nitro group, carboxyl group, ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and when X is S, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, and when X is O, ETU is a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

4. The organic light emitting diode of claim 1, wherein:
when X is S, the ETU is a substituted or unsubstituted pyridinyl group, a substituted or unsubstituted pyrimidinyl group, a substituted or unsubstituted triazinyl group, or a combination thereof, and
when X is O, the ETU is a substituted or unsubstituted pyridinyl group, a substituted or unsubstituted pyrimidinyl group, or a combination thereof.

5. The organic light emitting diode of claim 4, wherein:
when X is S, the ETU is a substituent represented by one of the following Chemical Formulae 6 to 10, and
when X is O, the ETU is a substituent represented by one of the following Chemical Formulae 7 to 10:

[Chemical Formula 6]

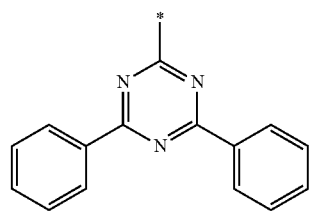

[Chemical Formula 7]

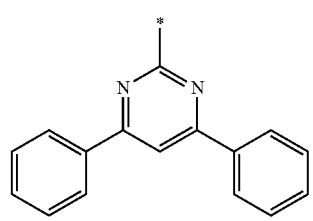

[Chemical Formula 8]

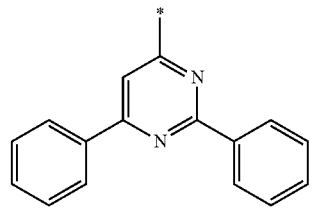

[Chemical Formula 9]

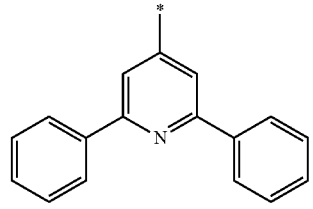

[Chemical Formula 10]

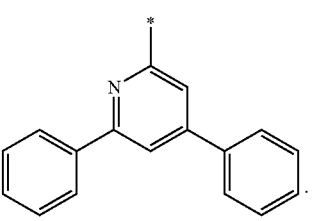

6. The organic light emitting diode of claim 1, wherein the compound for an organic optoelectronic device is represented by one of the following Chemical Formulae A-1 to A-18:

[Chemical Formula A-1]

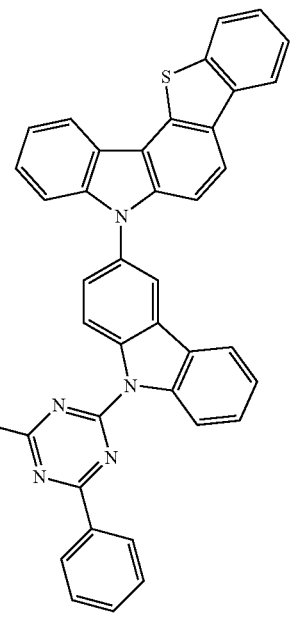

[Chemical Formula A-2]

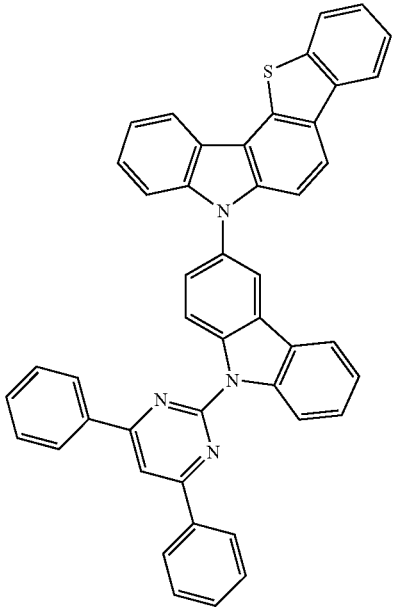

[Chemical Formula A-3]
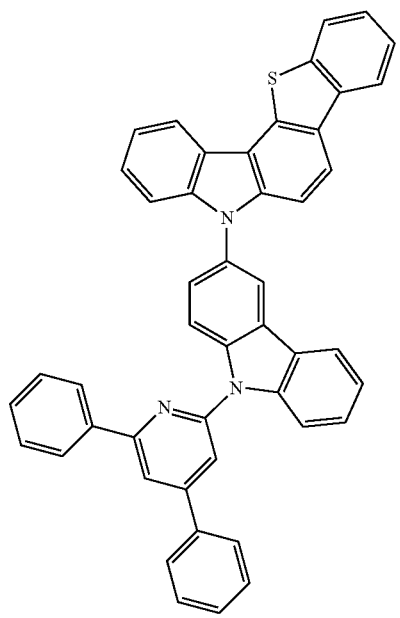
[Chemical Formula A-4]
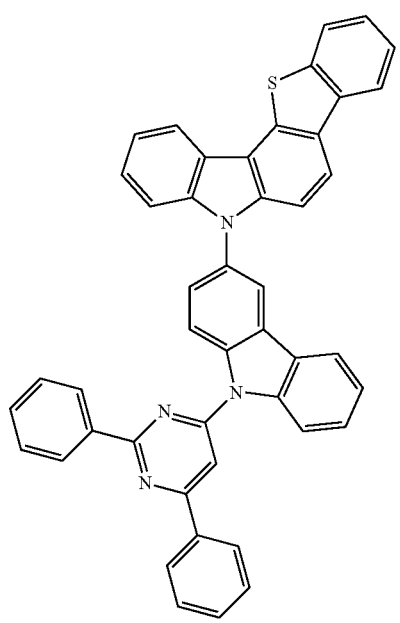
[Chemical Formula A-5]
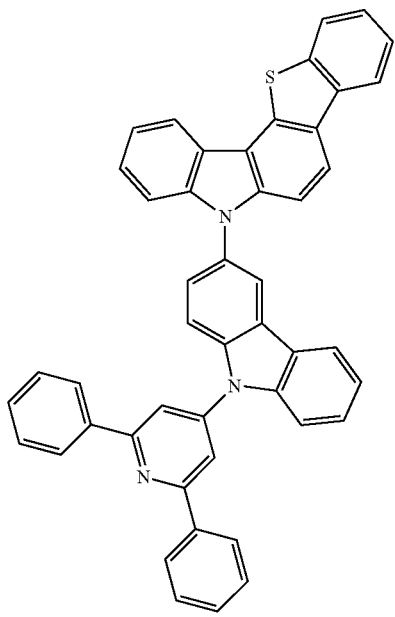
[Chemical Formula A-6]
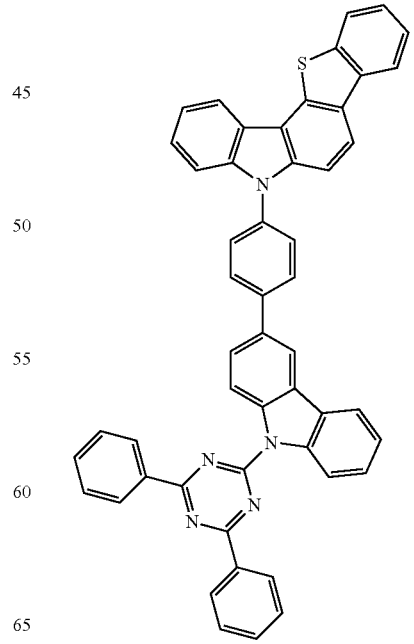

[Chemical Formula A-7]
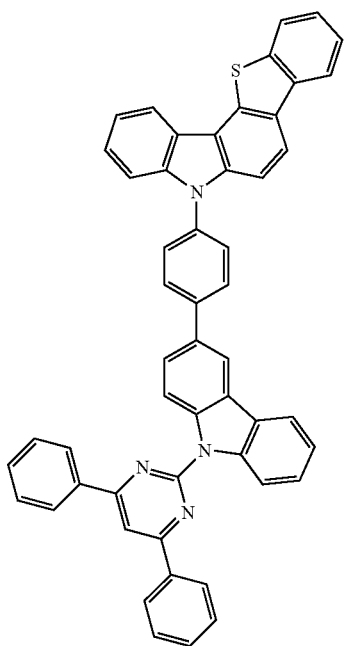
[Chemical Formula A-8]
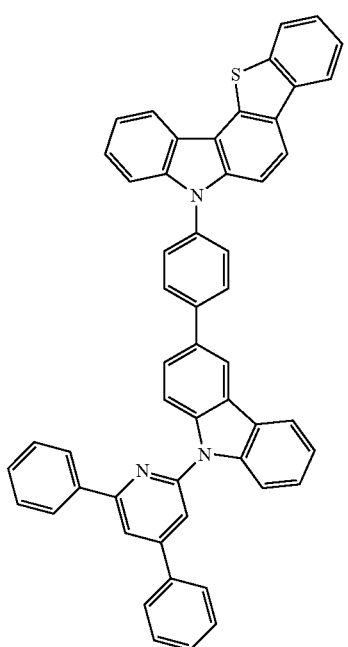
[Chemical Formula A-9]
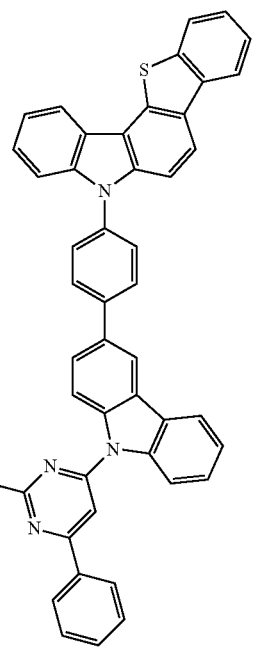
[Chemical Formula A-10]
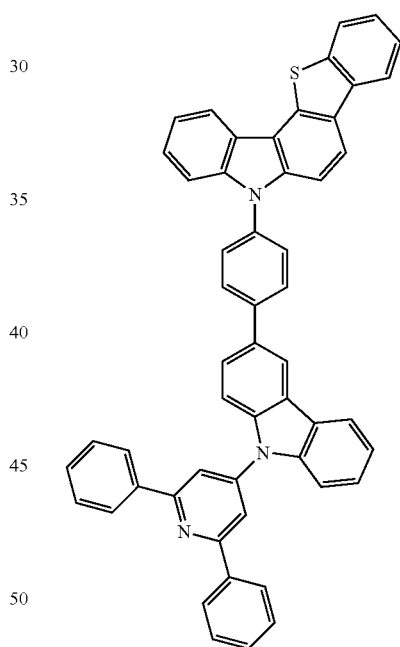
[Chemical Formula A-11]
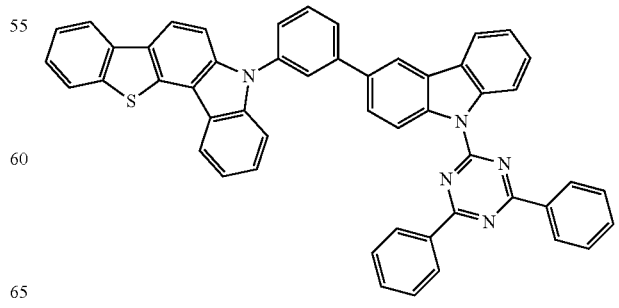

[Chemical Formula A-12]
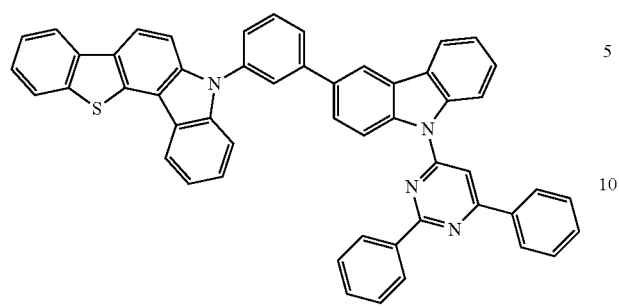
[Chemical Formula A-13]
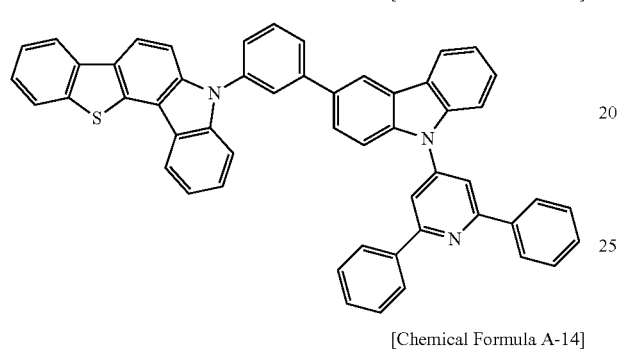
[Chemical Formula A-14]
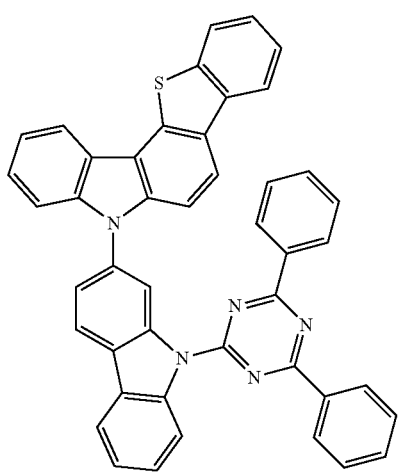
[Chemical Formula A-15]
[Chemical Formula A-16]
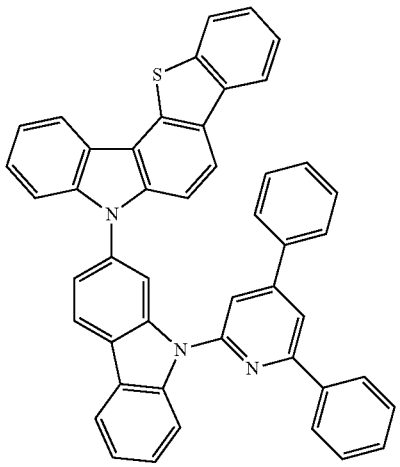
[Chemical Formula A-17]
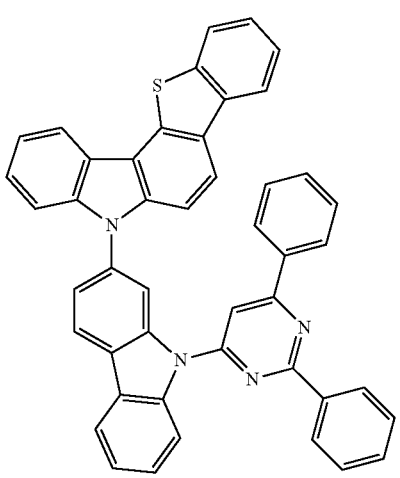
[Chemical Formula A-18]
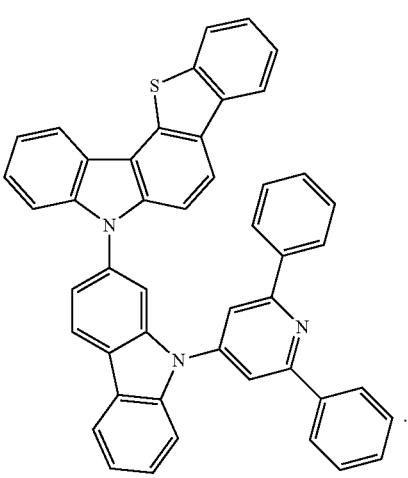
7. The organic light emitting diode of claim 1, wherein the compound for an organic optoelectronic device is represented by one of the following Chemical Formulae B-2 to B-4, B-7 to B-10, B-12, B-13, and B-15 to B-18:

[Chemical Formula B-2]
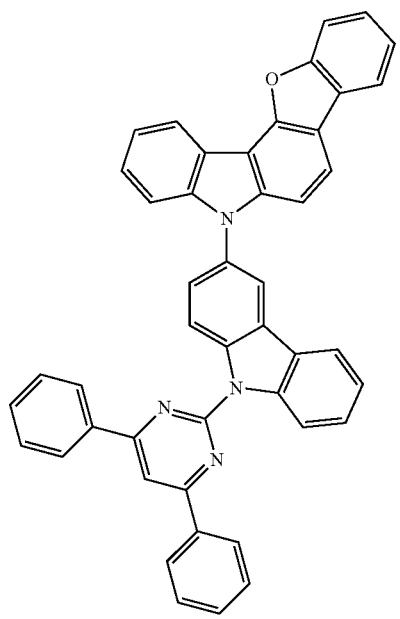
[Chemical Formula B-4]
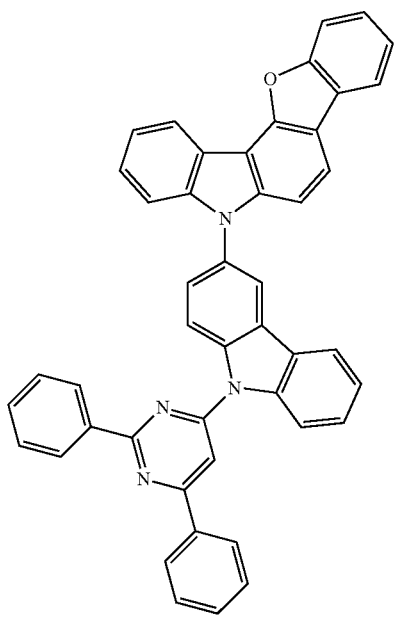
[Chemical Formula B-3]
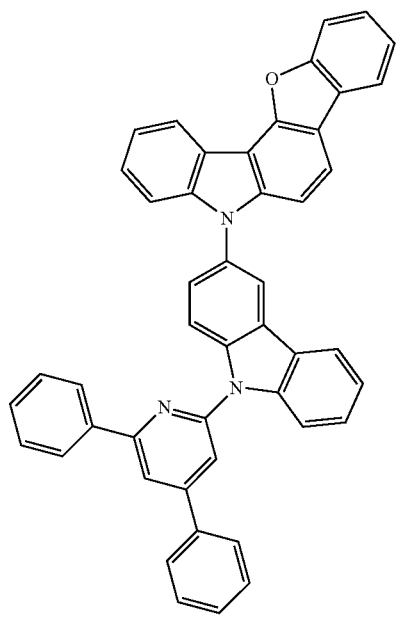
[Chemical Formula B-7]

[Chemical Formula B-8]
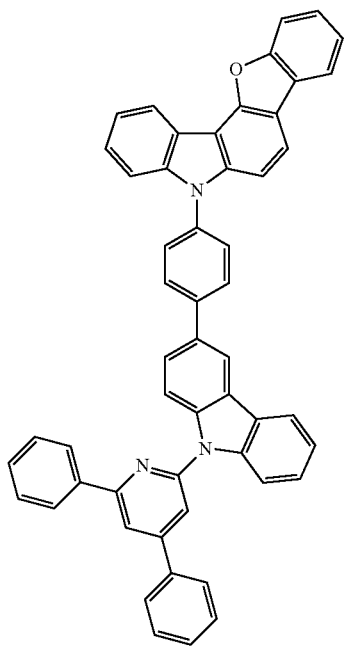
[Chemical Formula B-10]
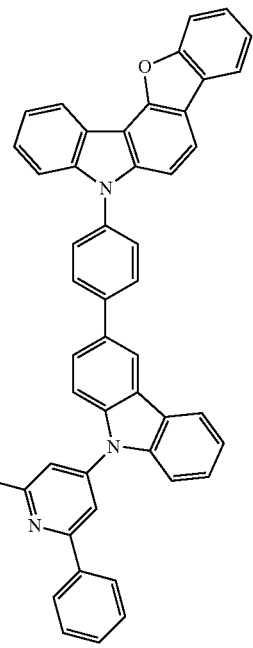
[Chemical Formula B-12]
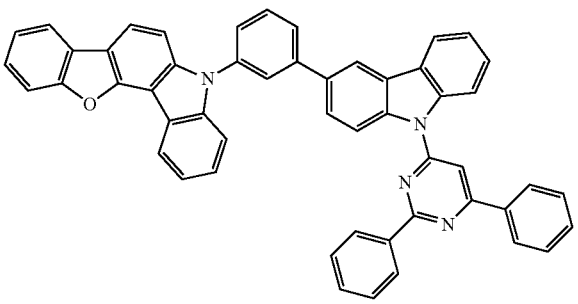
[Chemical Formula B-9]
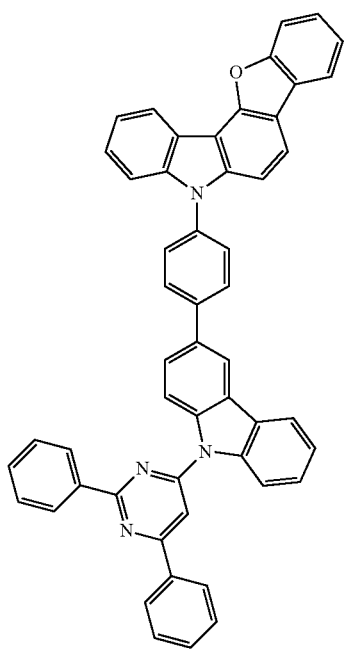
[Chemical Formula B-13]
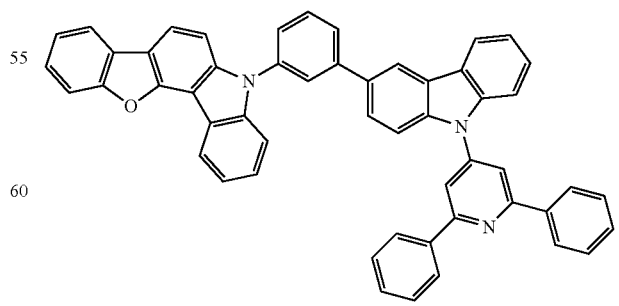

[Chemical Formula B-15]

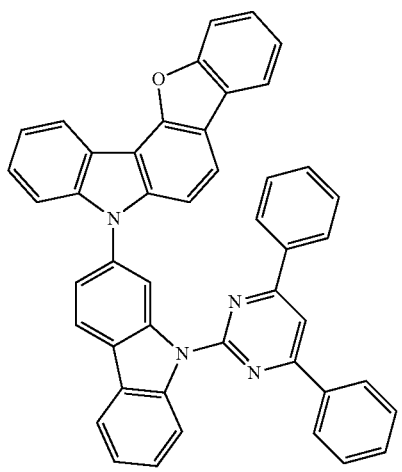

[Chemical Formula B-16]

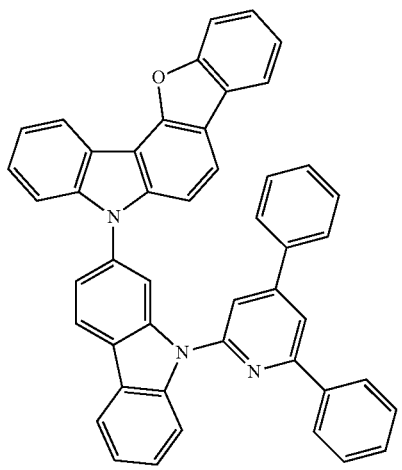

[Chemical Formula B-17]

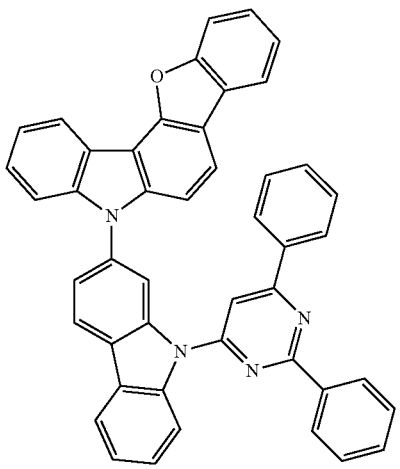

[Chemical Formula B-18]

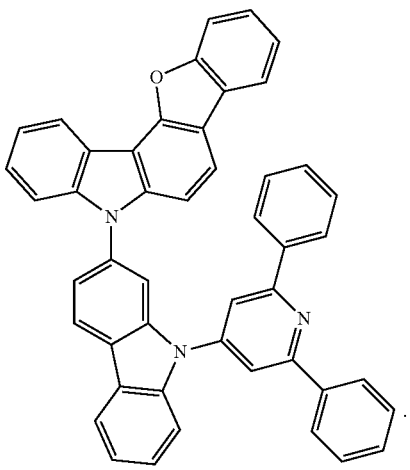

8. The organic light emitting diode of claim 1, wherein the organic thin layer further includes a hole transport layer, a hole injection layer, an electron transport layer, an electron injection layer, a hole blocking layer, and a combination thereof.

9. The organic light emitting diode of claim 8, wherein the compound for an organic optoelectronic device is included in the hole transport layer (HTL) or the hole injection layer (HIL).

10. A display device comprising the organic light emitting diode of claim 1.

* * * * *